US009101579B2

(12) United States Patent
Nguyen et al.

(10) Patent No.: US 9,101,579 B2
(45) Date of Patent: Aug. 11, 2015

(54) INHIBITION OF DRUG RESISTANT CANCER CELLS

(71) Applicant: Celgene Corporation, Summit, NJ (US)

(72) Inventors: Aaron N. Nguyen, San Jose, CA (US); Kyle J. MacBeth, San Francisco, CA (US); Jorge DiMartino, Belmont, CA (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/079,497

(22) Filed: Nov. 13, 2013

(65) Prior Publication Data

US 2014/0142043 A1 May 22, 2014

Related U.S. Application Data

(60) Provisional application No. 61/726,502, filed on Nov. 14, 2012, provisional application No. 61/793,638, filed on Mar. 15, 2013, provisional application No. 61/805,852, filed on Mar. 27, 2013.

(51) Int. Cl.
A61K 38/15 (2006.01)
A61K 45/06 (2006.01)
A61K 31/517 (2006.01)

(52) U.S. Cl.
CPC .............. A61K 38/15 (2013.01); A61K 31/517 (2013.01); A61K 45/06 (2013.01)

(58) Field of Classification Search
CPC ..... A61K 31/517; A61K 38/15; A61K 45/06; A61K 2121/00; A61K 2201/094
See application file for complete search history.

(56) References Cited

U.S. PATENT DOCUMENTS 4,328,245 A 5/1982 Yu et al.
4,409,239 A 10/1983 Yu et al.
4,410,545 A 10/1983 Yu et al.
4,977,138 A 12/1990 Okuhara et al.

(Continued)

FOREIGN PATENT DOCUMENTS

CA 2317003 8/2001
EP 0352646 1/1990

(Continued)

OTHER PUBLICATIONS

Gottesman (Annu. Rev. Med. 2002. 53:615-27).*

(Continued)

Primary Examiner — Louise Humphrey
Assistant Examiner — Tara Martinez
(74) Attorney, Agent, or Firm — Jones Day

(57) ABSTRACT

Provided herein are methods of treating cancer in a cancer patient by overcoming resistance of a cancer cell to a drug, or methods of overcoming resistance of a cancer cell to a drug, comprising administering to the patient an effective amount of (i) an EGFR tyrosine kinase inhibitor or a B-Raf kinase inhibitor, and (ii) an HDAC inhibitor. Also provided are methods for inhibiting or preventing proliferation of drug tolerant persister (DTP) cells comprising contacting these cells with an EGFR tyrosine kinase inhibitor or B-Raf kinase inhibitor in combination with an HDAC inhibitor. Yet also provided are methods for inhibiting or preventing formation of colonies of drug tolerant expanded persister (DTEP) cells comprising contacting these cells with an EGFR tyrosine kinase inhibitor or B-Raf kinase inhibitor in combination with an HDAC inhibitor.

6 Claims, 7 Drawing Sheets

(56) References Cited

U.S. PATENT DOCUMENTS

| | | | |
|---|---|---|---|
| 5,510,270 A | 4/1996 | Fodor et al. | |
| 5,545,522 A | 8/1996 | Van Gelder et al. | |
| 5,556,752 A | 9/1996 | Lockhart et al. | |
| 5,578,832 A | 11/1996 | Trulson et al. | |
| 5,595,756 A * | 1/1997 | Bally et al. | 424/450 |
| 5,605,793 A | 2/1997 | Stemmer | |
| 5,716,785 A | 2/1998 | Van Gelder et al. | |
| 5,776,905 A | 7/1998 | Gibbons et al. | |
| 5,830,721 A | 11/1998 | Stemmer et al. | |
| 5,837,458 A | 11/1998 | Minshull et al. | |
| 5,891,636 A | 4/1999 | Van Gelder et al. | |
| 6,117,679 A | 9/2000 | Stemmer | |
| 6,391,640 B1 | 5/2002 | Minshull et al. | |
| 6,403,555 B1 | 6/2002 | Skov et al. | |
| 6,548,479 B1 | 4/2003 | Skov et al. | |
| 6,706,686 B2 | 3/2004 | Long et al. | |
| 6,777,217 B1 | 8/2004 | Schreiber et al. | |
| 6,809,118 B2 | 10/2004 | Chung et al. | |
| 6,828,302 B1 | 12/2004 | Skov et al. | |
| 6,905,669 B2 | 6/2005 | DiMartino | |
| 6,946,441 B2 | 9/2005 | Long et al. | |
| 7,041,639 B2 | 5/2006 | Skov et al. | |
| 7,056,883 B2 | 6/2006 | Ito et al. | |
| 7,056,884 B2 | 6/2006 | Nakajima et al. | |
| 7,148,204 B2 | 12/2006 | Bennett et al. | |
| 7,171,311 B2 | 1/2007 | Dai et al. | |
| 7,314,862 B2 | 1/2008 | Naoe et al. | |
| 7,354,928 B2 | 4/2008 | Wang et al. | |
| 7,396,665 B2 | 7/2008 | Ueda et al. | |
| 7,470,722 B2 | 12/2008 | Malecha et al. | |
| 7,488,712 B2 | 2/2009 | Yoshida et al. | |
| 7,857,804 B2 | 12/2010 | McCaffrey et al. | |
| 2003/0162293 A1 | 8/2003 | Chu et al. | |
| 2004/0018968 A1 | 1/2004 | Sgouros et al. | |
| 2004/0053820 A1 | 3/2004 | Nakajima et al. | |
| 2004/0072735 A1 | 4/2004 | Richon et al. | |
| 2004/0077591 A1 | 4/2004 | Dangond | |
| 2004/0127523 A1 | 7/2004 | Bacopoupos et al. | |
| 2004/0228909 A1 | 11/2004 | Sarris et al. | |
| 2005/0059682 A1 | 3/2005 | Rubinfeld | |
| 2005/0070467 A1 | 3/2005 | Naoe et al. | |
| 2005/0187148 A1 | 8/2005 | Naoe et al. | |
| 2005/0187149 A1 | 8/2005 | Naoe et al. | |
| 2005/0191713 A1 | 9/2005 | Sasakawa et al. | |
| 2005/0222013 A1 | 10/2005 | Jung et al. | |
| 2005/0272647 A1 | 12/2005 | Yamaji et al. | |
| 2006/0018921 A1 | 1/2006 | Levenson et al. | |
| 2006/0019883 A1 | 1/2006 | Kronblad et al. | |
| 2006/0100140 A1 | 5/2006 | Dent et al. | |
| 2006/0106049 A1 | 5/2006 | Odenike | |
| 2006/0128660 A1 | 6/2006 | Rajski et al. | |
| 2006/0135413 A1 | 6/2006 | Naoe et al. | |
| 2006/0223747 A1 | 10/2006 | Ito et al. | |
| 2006/0270016 A1 | 11/2006 | Holm | |
| 2007/0015787 A1 | 1/2007 | Bruncko et al. | |
| 2007/0110719 A1 | 5/2007 | Holm | |
| 2007/0129290 A1 | 6/2007 | Or et al. | |
| 2007/0148228 A1 | 6/2007 | Cumming et al. | |
| 2007/0292512 A1 | 12/2007 | Leonard et al. | |
| 2008/0214446 A1 | 9/2008 | Okada et al. | |
| 2008/0233562 A1 | 9/2008 | Sasakawa et al. | |
| 2009/0186382 A1 | 7/2009 | Verdine et al. | |
| 2009/0209616 A1 | 8/2009 | Verdine et al. | |
| 2009/0221473 A1 | 9/2009 | Chan et al. | |
| 2009/0311175 A1 * | 12/2009 | Brose | 424/1.61 |
| 2010/0093610 A1 | 4/2010 | Vrolijk et al. | |

FOREIGN PATENT DOCUMENTS

| | | |
|---|---|---|
| EP | 1010705 | 6/2000 |
| EP | 1426054 | 6/2004 |
| JP | 7(1995)-64872 | 7/1995 |
| JP | 11-335375 | 12/1999 |
| JP | 2001-348340 | 12/2001 |
| WO | WO 98/39965 | 9/1998 |
| WO | WO 98/40080 | 9/1998 |
| WO | WO 01/18171 | 3/2001 |
| WO | WO 01/42282 | 6/2001 |
| WO | WO 02/06307 | 1/2002 |
| WO | WO 02/15921 | 2/2002 |
| WO | WO 02/20817 | 3/2002 |
| WO | WO 02/86498 | 4/2002 |
| WO | WO 02/97053 | 5/2002 |
| WO | WO 02/055017 | 7/2002 |
| WO | WO 02/055688 | 7/2002 |
| WO | WO 02/085400 | 10/2002 |
| WO | WO 02/090534 | 11/2002 |
| WO | WO 03/015810 | 2/2003 |
| WO | WO 03/017763 | 3/2003 |
| WO | WO 03/024442 | 3/2003 |
| WO | WO 03/035843 | 5/2003 |
| WO | WO 03/053468 | 7/2003 |
| WO | WO 03/070188 | 8/2003 |
| WO | WO 03/083067 | 10/2003 |
| WO | WO 03/084611 | 10/2003 |
| WO | WO 03/088954 | 10/2003 |
| WO | WO 03/103613 | 12/2003 |
| WO | WO 2004/009771 | 1/2004 |
| WO | WO 2004/017996 | 3/2004 |
| WO | WO 2004/024160 | 3/2004 |
| WO | WO 2004/062654 | 7/2004 |
| WO | WO 2004/064727 | 8/2004 |
| WO | WO 2004/074478 | 9/2004 |
| WO | WO 2004/096289 | 11/2004 |
| WO | WO 2004/098495 | 11/2004 |
| WO | WO 2005/000282 | 1/2005 |
| WO | WO 2005/000289 | 1/2005 |
| WO | WO 2005/000332 | 1/2005 |
| WO | WO 2005/009961 | 2/2005 |
| WO | WO 2005/018578 | 3/2005 |
| WO | WO 2005/023179 | 3/2005 |
| WO | WO 2005/027842 | 3/2005 |
| WO | WO 2005/030239 | 4/2005 |
| WO | WO 2005/051430 | 6/2005 |
| WO | WO 2005/052143 | 6/2005 |
| WO | WO 2005/053609 | 6/2005 |
| WO | WO 2005/058298 | 6/2005 |
| WO | WO 2005/079827 | 9/2005 |
| WO | WO 2005/085864 | 9/2005 |
| WO | WO 2005/087206 | 9/2005 |
| WO | WO 2005/105055 | 11/2005 |
| WO | WO 2005/105066 | 11/2005 |
| WO | WO 2005/115149 | 12/2005 |
| WO | WO 2005/117930 | 12/2005 |
| WO | WO 2006/027346 | 3/2006 |
| WO | WO 2006/055621 | 5/2006 |
| WO | WO 2006/060382 | 6/2006 |
| WO | WO 2006/060429 | 6/2006 |
| WO | WO 2006/099396 | 9/2006 |
| WO | WO 2006/129105 | 12/2006 |
| WO | WO 2007/009539 | 1/2007 |
| WO | 2007040522 | 4/2007 |
| WO | WO 2007/040522 | 4/2007 |
| WO | WO 2007/058896 | 5/2007 |
| WO | WO 2007/061939 | 5/2007 |
| WO | WO 2007/145704 | 12/2007 |
| WO | WO 2007/146730 | 12/2007 |
| WO | WO 2008/013589 | 1/2008 |
| WO | WO 2008/027837 | 3/2008 |
| WO | WO 2008/127659 | 10/2008 |
| WO | WO 2009/015229 | 1/2009 |

OTHER PUBLICATIONS

Sporn et al. ("Chemoprevention of Cancer," Carcinogenesis, vol. 21 (2000), 525-530).*

Auerbach et al. (Cancer and Metastasis Reviews, 2000, 19: 167-172).*

Gura T (Science, 1997, 278(5340): 1041-1042, encloses 1-5).*

Pierarz et al (51st ASH Annual Meeting and Exposition, online program and abstract, Dec. 3, 2009-Final Results of a Phase 2 NCI Multicenter Study of Romidepsin in patients with Relapsed Peripheral T-Cell Lymphoma (PTCL).*

(56) References Cited

OTHER PUBLICATIONS

Thaler et al. (Expert Opin. Drug Discovery, Apr. 2011;6(4):393-404).*
Lachenmayer et al. (Combination therapy for hepatocellular carcinoma: Aditive preclinical efficacy of the HDAC inhibitor panobinostat with sorafenib; Journal of Hepatology; 2012 vol. 56;1343-1350).*
Aron et al., "Depsipeptide (FR901228) induces histone acetylation and inhibition of histone deacetylase in chronic lymphocytic leukemia cells concurrent with activation of caspase 8-mediated apoptosis and down- regulation of c-FLIP protein." Blood, 102(2):652-658 (2003).
Bates et al., "Final Clinical Results of a Phase 2 NCI Multicenter Study of romidepsin In Recurrent Cutaneous T-Cell Lymphoma (Molecular Analyses Included)," ASH Annual Meeting Abstracts, 112(11): p. 1568 (2008).
Berge et al., "Pharmaceutical Salts," J Pharm Science 66:1-19, 1977.
Bhalla, "Epigenetic and chromatin modicifers as targeted therapy of hematologic malignancies," Clin Oncol, 23(17):3971-3993 (2005).
Bishton et al., "Epigenetic target in hematological malignancies: combination therapies with HDAC's and demethylating agents," Expert Rev Anticancer Ther, 7(10):1439-1449 (2007).
Bogden et al., "Growth of Human Tumor Xenografts Implanted under the Renal Capsule of Normal Immunocompetent Mice," Exp Cell Biol 47:281-293 (1979).
Bolden et al., "Anticancer activities of histone deacetylase inhibitors," Nat Rev Drug Discovery, 5(9):769-784 (2006).
Budillon et al., "Growth arrest, apoptosis and potentiation of 5-fluorouracil and Raltitrexed cytotoxic effect induced by histone deacetylase inhibitor SAHA in colorectal cancer cells," Eur J Cancer 38:S29 (2002).
Butler et al., "Suberoylanilide Hydroxamic Acid, an Inhibitor of Histone Deacetylase, Suppresses the Growth of Prostate Cancer Cells in Vitro and in Vivo," Cancer Res 60:5165-5170 (2000).
Byrd et al., "A phase 1 and pharmacodynamic study of depsipeptide (FK228) In chronic lymphocytic leukemia and acute myeloid leukemia," Blood, 105(3):959-967 (2005).
Byrd et al., "Depsipeptide (FR901228): a novel therapeutic agent with Selective in vitro activity against human B-cell chronic lymphocytic leukemia cells," Blood, 94(4):1401-1408 (1999).
Cara et al., "Retreatment of patients with the same chemotherapy: Implications for clinical mechanisms of drug resistance," Ann. Oncol., 12:23-37 (2001).
Catley et al., "Aggresome induction by proteasome inhibitor bortezpmib and {alpha}-tubulin hyperacetylation by tubulin deacetylase (TDAC) inhibitor LBH589 are synergistic in myeloma cells," Blood 108(10):3441-3449 (2006).
Chan et al., "Depsipeptide (FR901228, NSC-630176) pharmacokinetics in the rat by LC/MS/MS," Invest New Drugs,15(3):195-206 (1997).
Cheson et al., "New Drugs for the Treatment of Chronic Lymphocytic Leukemia" Reviews Clin Exp Hematol 4(2):145-166 (2000).
Conway et al., "Vincristine-and Cisplatin-induced Apoptosis in Human Retinoblastoma. Potentiation by Sodium Butyrate," Eur J Cancer, 34(11):1741-1748 (1998).
Dai et al., "Interactions between bortezomib and romidepsin and belinostat in chronic lymphocytic leukemia cells ," Clin Cancer Res, 14(2):549-558 ( 2008).
Database Biosis Online, AN-PREV200400024248, XP-002342749, "Anti-Tumor Efficacy of Four Different Histone Deacetylase inhibitors on Hepatoma Cells in Vitro", 2003 (Abstract No. T1786).
Dokmanovic & Marks, "Prospects: histone deacetylase inhibitors," J Cell Biochem, 96(2):293-304 (2005).
Fiebig et al., "Bcl-XL is qualitatively different from and ten times more effective than Bcl-2 when expressed in a breast cancer cell line," Cancer, 6:213 (2006).
Findley et al., "Expression and Regulation of Bcl-2, Bcl-xl, and Bax Correlate With p53 Status and Sensitivity to Apoptosis in Childhood Acute Lymphoblastic Leukemia," Blood, 89(8): 2986-2993 (1997).
Finnin et al., "Structures of a histone deacetylase homologue bound to the TSA and SAHA Inhibitors," Nature, 401(6749):188-193 (1999).
Fischer et al., $41^{st}$ Annual Meeting of the American Society of Clinical Oncology, Abstr # 3106 (2005).
Fukumura et al., "A sensitive transcriptome analysis method that can detect unknown transcripts," Nucl Acids Res 31(16):e94 (2003).
Furumai et al.,"FK228 (depsipeptide) as a natural prodrug that inhibits class I histone deacetylases," Cancer Res, 62(17):4916-4921 (2002).
Garcia-Manero et al., "Phase 1/2study of the combination of 5-aza-2'-deoxycytidine with valporic acid in patients with leukemia," Blood, 108(10):3271-3279 (2006).
Geldof et al., "Cytotoxicity and neurocytoxicity of new marine anticancer agents evalucated using in vitro assays," Cancer Chemother & Pharmacol 44(4):312-318 (1999).
Glasspool et al., "Epigenetics as a mechanism driving polygenic clinical drug resistance," Br. J. Cancer, 94:1087-1092 (2006).
Gore et al., "Combined DNA methyltransferase and histone deacetylase inhibition in the treatment of myeloid neoplasms," Cancer Res, 66(12):6361-6369 (2006).
Gore et al., "Impact of the putative differentiating agent sodium phenylbutyrate on myelodysplastic syndromes and acute myeloid leukemia," Clin Cancer Res, 7(8):2330-2339 (2001).
Han et al., "Apicidin, a Histone Deacetylase Inhibitor Inhibits Proliferation of Tumor Cells via Induction of p21 WAF1/Cip1 and Gelsolin," Cancer Res 60(21):6068-6074 (2000).
Harrison et al., "High Response Rates with the Combination of Bortezomib, Dexamethasone and the Pan-Histone Deacetylase Inhibitor Romidepsin In Patients with Relapsed or Refractory Multiple Myeloma In Phase I/II Clinical Trial," ASH Annual Meeting Abstracts, 112(11):3698 (2008).
Inoue et al., "Subrenal capsule assay-an experimental study and clinical application to chemosensitivity tests," Gan to Kagaku Ryoho 14(5Pt2):1629-1635 (1987) (Abstract).
Jones & Baylin, "The Epigenomics of Cancer," Cell 128:683-692 (2007).
Jones & Baylin, "The fundamental role of epigenetic events in Cancer," Nat Rev Genet, 3(6):415-428 (2002).
Jung et al., "Amide Analogues of Trichostatin A as Inhibitors of Histone Deacetylase and Inducers of Terminal Cell Differentiation," J Med Chem US 42(22):4669-4679 (1999).
Kahn et al., "Total Synthesis of the Antitumor Depsipeptide FR-901,228," J Am Chem Soc 118:7237-7238,(1996).
Kano et al., "The Joint Meeting of the $64^{th}$ Annual Meeting of the Japanese Society of Hematology and the $44^{th}$ Annual Meeting of the Japanese Society of Clinical Hematology," Japanese J Clin Hematology 43(8):116 (2002).
Kawamoto et al., "Expression Profiling by iAFLP: A PCR-Based Method Or Genome-Wide Gene Expression Profiling," Genome Res 12:1305-1312 (1999).
Khan et al., "Analysis of histone deacetylase inhibitor, depsipeptide (FR901228), effect on multiple myeloma ," Br J Haematol, 125(2):156-161 (2004).
Kim et al., "Clinically significant responses Achieved with Romidepsin in Treatment-Refractory Cutaneous T-Cell Lymphoma: Final Results from a Phase 2B, International, Multicenter, Registration Study," ASH Annual Meeting Abstracts, 112(11):263 (2008).
Kisselev & Goldberg, "Proteasome inhibitors: from research tools to drug candidates," Chem Biol 8:739-758 (2001).
Kitazono et al., "Adenovirus HSV-TK Constuct with Thyroid-Specific Promoter: Enhancement of Activity and Specificity with Histone Deacetylase Inhibitors and Agents Modulating the Camp Pathway," Int J Cancer 99:453-459 (2002).
Kitazono et al., "Enhanced Adenovirus Transgene Expression in Malignant Cells Treated with the Histone Deacetylase Inhibitor FR901228," Cancer Res 61:6328-6330 (2001).
Kitazono et al., "Low Concentrations of the Histone Deacetylase Inhibitor, Depsipeptide (FR901228), Increase Expression of the Na/I Symporter and Iodine Accumulation in Poorly Differentiated Thyroid Carcinoma Cells," J Clin Endocrin 86(7):3430-3435 (2001).
Kitazono et al., Proc Amer Assoc Cancer Res Annual 43:799 (2002) (Abstract only).

(56) References Cited

OTHER PUBLICATIONS

Klimek et al., "Tolerability, pharmacodynamics, and pharmacokinetics studies fo depsipeptide (romidepsin) in patients with acute myelogenous leukemia or advanced myelodysplastic syndromes," Clin Cancer Res, 14(3):826-832 (2008).
Klisovic et al., "Depsipeptide (FR9801228) Inhibits Proliferation and Induces Apoptosis in Primary and metastatic Human Uveal Melanoma Cell Lines," Invest Ophthalmol Vis Sci, 44(6):2390-2398 (2003).
Komatsu et al., "Cyclic Cyfroxamic-acid-containing Peptide 31, a Potent Syntheic Histone Deacetylase Inhibitor with Antitumor Activity," Cancer Res 61(11):4459-4466 (2001).
Kosugi et al., "In vivo Effects of a Histone Deacetylase Inhibitor, FK228, on Human Acute Promyelocytic Leukemia in NOD/Shi-scid/scid Mice," Japanese J Cancer Res 92(5):529-536 (2001).
Kuendgen et al., "Treatment of myelodysplastic syndromes with valproic acid alone or in combination with all-trans retinoic acid," Blood, 104(5):1266-1269 (2004).
Kurata et al., "Effect of re-treatment with gefitinib ('Iressa', ZD1839) after acquisition of resistance," Ann. Oncol., 15:173-174 (2004).
Kurtze et al., "KRAS-mutated non-small cell lung cancer cells are responsive to either co-treatment with erlotinib or gefitinib and histone deacetylase inhibitors or single treatment with lapatinib," Oncology Reports, 25(4):1021-1029 (2011).
Liakopoulou et al., "Stimulation of Fetal Hemoglobin Production by Short Chain Fatty Acids," Blood, 86:3227 (1995).
Maeda et al., "Up-regulation of costimulatory/adhesion molecules by histone deacetylase ihibitors in acute myeloid leukemia cells," Blood, 96(12):3847-3856 (2000).
Magner et al., "Activation of MHC class I, II, and CD40 gene expression by histone deacetylose inhibitors ," J Immunol, 165(12):7017-7024 (2000).
Marks et al., "Histone deacetylase inhibitors: Inducers of differentiation or apoptosis of transformed cells," J Natl Cancer Inst, 92(15):1210-1216 (2000).
Marshall et al., "A phase I trial of depsipeptide (FR901228) in patients with advanced cancer ," J Exp Ther Oncol, 2(6):325-332 (2002).
Mertins et al., Proc Amer Assoc Cancer Res Annual Meetins 40:623 (1999).
Mitsiades et al., "Transcriptional signature of stone deacetylase inhibition in multiple myeloma: biological and clinical implications," Proc Natl Acad Sci USA, 101(2):540-545 (2004).
Molife et al., "Phase II study of FK228 in patients with hormone refractory prostate cancer (HRPC)," J Clin Oncol (Meeting Abstracts), 24(18 Suppl):14554 (2006).
Murata et al., "Apoptotic Cytotoxic Effects of a Histone Deacetylase Inhibitor, FK228, on Malignant Lymphoid Cells," Japanese J Cancer Res 91:1154-1160 (2000).
Nakajima et al., ", FR901228, a potent antitumor antibiotic, is a novel histone detlcetylose inhibitor," Exp Cell Res, 241(1)126-133 (1998).
Trumpp et al., "Mechanisms of Disease: cancer stem cells-targeting the evil twin," Nat. Clin. Prac. Oncol., 5:337-347 (2008).
Nebbioso et al., "Tumor-selective action of HDAC inhibitors involves TRAIL induction in acute myeloid leukemia cells," Nat Med, 11(1):77-84 (2005).
Nebozhyn et al., "Quantitative PCR on 5 genes reliably Identifies CTCL patients with 5% to 99% circulating tumor cells with 90% accuracy," Blood, 107(8):3189-3196 (2006).
Newbold et al., "Characterisation of the novel apoptotic and therapeutic activities of the histone deacetylase inhibitor romidepsin," Mol Cancer Ther, 7(5):1066-1079 (2008).
Niesvizky et al., "Multicenter Phase II Trial of the Histone Deacetylase Inhibitor Depsipeptide (FK228) for the Treatment of Relapsed or Refractory Multiple Myeloma (MM)," Blood ASH Annual Meeting Abstracts, 106(11):2574 (2005).
Nishimura et al., "A New Antitumor Antibiotic, FE900840," J Antibiot XLII(4):553-557 (1989).
Norng et al., "The HDAC inhibitor romidepsin prevents the emergence of drug-tolerant cancer cells," AACR Annual Meeting (2013).

Nuijen et al., "Development of a lyophilized parenteral pharmaceutical formulation the investicational polypeptide marine anticancer agent kahalalide F.," Medline (2001) XP-002206588.
Odenike et al., "Histone deacetylase inhibitor romidepsin has differential activity in core binding factor acute myeloid leukemia," Cancer Res, 14(21):7095-7101 (2008).
Paoluzzi et al., "Romidepsin and belinostat synergize the antineoplastic effect of bortezomib in mantle cell lymphoma," Clin Cancer Res, 16(2):554-565 (2010).
Peart et al., "Identification and functional significance of genes regulated by structurally different histone deacetylose inhibitors," Proc Natl Acad Sci USA, 102(10):3697-3702 (2005).
Peart et al., "Novel mechanisms of apoptosis induced by histone deacetylase inhibitors," Cancer Res, 63(15):4460-4471 (2003).
Pei et al.. "Syneraistic induction of oxidative injury and apoptosis in human multiple myeloma cells by the proteasome inhibitor bortezpmib and histone deacetylase inhibitors," Clin Cancer Res, 10(11):3839-3852 (2004).
Piekarz et al., "A Review of Depsipeptide and Other Histone Deacetylase Inhibitors in Clinical Trials," Curr Pharm Des 10:2289-2298 (2004).
Piekarz et al., "Cardiac studies In patients treated with depsipeptide, FK228,1 n a phase II trial for T-cell lymphoma," Clin Cancer Res, 12(12):3762-3773 (2006).
Piekarz et al., "Completion of the First Cohort of Patients with Cutaneous T-Cell Lymphoma Enrolled on a Phase II Trial of Depsipeptide," ASH Annual Meeting Abstracts,106(11):231 (2005).
Piekarz et al., "Epigenetic modifiers: basic understanding and clinical development," Clin Cancer Res, 15(12):3918-3926 (2009).
Piekarz et al., "Inhibitor of histone deactylation, depsipeptide (FR901228), in the treatment of peripheral and cutaneous T-cell lymphoma: a case report," Blood, 98(9):2865-2868 (2001).
Piekarz et al., "Phase II Multi-Institutional Trial of the Histone Deacetylase Inhibitor Romidepsin As Monotherapy for Patients With Cutaneous T-Cell Lymphoma," J Clin Oncol, 27(32):5410-5417 (2009).
Piekarz et al., "Results of a Phase 2 NCI Multicenter Study of Romidepsin in Patients with Relapsed Peripheral T-Cell Lymphoma (PTCL)," ASH Annual Meeting Abstracts 112(11):1567 (2008).
Piekarz et al., "T-cell lymphoma as a model for the use of histone deacetylase inhibitors in cancer therapy: impact of depsipeptide on molecular markers, therapeutic targes, and mechanisms of resistance," Blood, 103(12):4636-4643 (2004).
Piekarz, R., et al, "Update of the NCI multiinstutional phase II trial of romidepsin, FK228,for patients with cutaneous or peripheral T-cell lymphoma,". J Clio Oncol (Meeting Abstracts), 2007.25(18_suppl): p. 8027 (2007).
Prince et al., "Clinical studies of histone deacetylase inhibitors," Clin Cancer Res, 15(12):3958-3969 (2009).
Program of the 4th Japanese Foundation for Cancer Research, International Symposium on Cancer Therapy (ISCC), Feb. 12, 1999.
Rasheed et al., "Histone deacetylase inhibitors in cancer therapy," Expert Opin Investig Drugs, 16(5):659-678 (2007).
Redmond et al., "Resistance mechanisms to cancer chemotherapy," Front Biosci., 13:5138-5154(2008).
Richon et al., "Histone Deacetylase Inhibitors: A New Class of Potential Therapeutic Agents for Cancer Treatment," Clin Cancer Res 8(3):662-664 (2002).
Richon et al., "Histone deacetylasei inhibitor selectively induces p21WAFI expression and gene-associated histone acetylation," Proc Natl Acad Sci USA, 97(18):10014-10019 (2000).
Robey et al., "Increased MDRI expression in normal and malignant peripheral blood mononuclear cells obtained from patients receiving depsipetide•(FR901228, FK228, NSC630176)," Clin Cancer Res, 12(5):1547-1555 (2006).
Roychowdhury et al., "Selective efficacy of depsipeptide in a xenograft model of Epstein-Barr virus-positive lymphoproliferative disorder," J Natl Cancer Inst, 96(19):1447-1457 (2004).
Sakai et al., "MBD3 and HDACI,two components of the NuRDcomplex, are localized at Aurora-A-positive centrosomes in M phase," J Biol Chem, 277(50):48714-48723 (2002).

(56) References Cited

OTHER PUBLICATIONS

Sandor et al., "P21-dependent G arrent with downregulation of cyclin D1 upregulation of cyclin E by the histone deacetylase inhibitor FR901228," Br J Cancer 83(6):817-825, (2000).
Sandor et al., "Phase I trial of the histone deacetylase Inhibitor, depsipeptide (FR901228, NSC 630176), In patients with refractory neoplasms," Clin Cancer Res, 8(3):718-728 (2002).
Sasakawa et al., "Effects of FK228, a novel histone deacetylase inhibitor, on human lymphoma U-937 cells in vitro and in vivo," Biochem Pharmacol, 64(7):1079-1090 (2002).
Sawa et al., "Anti-tumor effects of Hitone deacetylase inhibitors against human glioma cells," Proc of Japanese Cancer Assoc 60:597 (2001) (w/English translation).
Sawa et al., "Histone deacetylase Inhibitor, FK228, Induces apoptosis and suppresses cell roliferation of human glioblastoma cells In vitro and In vivo," Acta Neuropathol (Berlin), 07(6):523-531 (2004).
Schrump et al., "Clinical and molecular responses in lung cancer patients receiving romidepsin," Clin Cancer Res, 14(1):188-198 (2008).
Schwartsmann et al., "Marine organisms as a source of new anticancer agents," The Lancet Oncology 2(4):221-225 (2001).
Sharma et al., "A chromatin-mediated reversible drug-tolerant state in cancer cell subpopulations," Cell, 141:69-80 (2010).
Sreedharan et al., "Relevance of circadian closing time for the tolerability of germcitabine as a single agent of combined with cisplatin in mice," Proc Amer Assoc Cancer Res 44(2 ed.):742 (2003) (XP-001154773).
Stadler et al., "A phase II study of depsipeptide in refractory metastatic renal cell cancer" Clin Genitourin Cancer, 5(1):57-60 (2006).
Su et al., "A phase II study of single agent depsipeptide (DEP) in patients (pts) with radioactive iodine (RAI)-refractory, metastatic,thyroid carcinoma: Preliminary toxicity and efficacy experience," J Clin Oncol (Meeting Abstracts), 24(18 Suppl):5554 (2006).
Sutheesophon et al., "Histone deacetylase inhibitor depsipeptide (FK228) induces apoptosis in leukemic cells by facilitating mitochondrial translocation of Bax, which is enhanced by the proteasome Inhibitor bonezpmib," Acta Haematol, 115(1-2):78-90 (2006).
Thurn et al., "Rational therapeutic combinations with histone deacetylase inhibitors for the treatment of cancer," Future Oncology, 7(2):263-283 (2011).
Ueda et al., "Action of FR901228, a novel antitumor bicyclic depsipeptide produced by *Chromobacterium violaceum* No. 968, on Ha-ras transformed NIH3T3 cells," Biosci Biotechnol Biochem, 58(9):1579-1583 (1994).
Ueda et al., "Expression of a full-length cDNA for the human "MDR1" gene confers resistance to colchicines, doxorubicin, and vinblastine," PNAS USA 84:3004 (1987).
Ueda et al., "FR901228, a novel antitumor bicyclic depsipeptide produced by *Chromobacterium violaceum* No. 968. I. Taxonomy, fermentation, isolation, physico-chemical and biological properties, and antitumor activity," J Antibiot (Tokyo),47:301-310, (1994).
Ueda et al., "FR901228, A Novel Antitumor Bicyclic Depsipeptide Produced by *Chromobacterium violaceum* No. 968," J Antibiot (Tokyo) 47:315-323 (1994).
Vrana et al., "Induction of apoptosis in U937 human leukemia cells by suberoylanilide hydroxamic acid (SAHA) proceeds through pathways that are regulated by Bcl-2:Bcl-XL, c-Jun, and p21CIPI, but independent of p53," Oncogene, 18(50):7016-7025 (1999).
Wang et al., "Fungal metabolite FR901228 inhibits c-Myc Fas ligand expression," Oncogene 17:1503-1508 (1998).
Watanabe et al., "Induction of autophagy in malignant rhabdoid tumor cells by the histone deacetylase inhibitor FK228 through AIF translocation," Int J Cancer, 124(1):55-67 (2009).
Weidle et al. "Inhibition of Histone Deacetylases: a New Strategy to Target Epigentic Modifications for Anticancer Treatment," Anticancer Res 20:1471-1486 (2000).
Whitehead et al., "Phase II trial of depsipeptide (NSC-630176) in colorectal cancer patients who have received either one or two prior chemotherapy regimens for nwrARrux or locally advanced, unresectable disease: A Southwest Oncology Group study," J Clin Oncol (Meeting Abstracts), 24(18 Suppl):3598 (2006).
Whittaker et al., "International multicenter phaSe II study of the HDAC inhibitor (HDAC) depsipeptide (FK228) in cutaneous T-cell lymphoma (CTCL): Interim report," J Clin Oncol (Meeting Abstracts), 24(18 Suppl):3063 (2006).
Xiao et al., "Efflux of Depsipeptide FK228(FR901228, NSC-630176) Is Mediated by P-Glycoprotein and Multidrug Resistance-Associate Protein 1," J Pharm & Exp Therapeutics 313(1):268-276 (2005).
Xiao et al., "Identification of thiols and glutathione conjugates of depsipeptide FK228 (FR901228), a novel hostone protein deacetylase inhibitor, in the blood," Rapid Commun Mass Spectrom 17:757-766 (2003).
Yano et al., "Retreatment of Lung Adenocarcinoma Patients With Gefitinib Who Had Experienced Favorable Results From Their Initial Treatment With This Selective Epidermal Growth Factor Receptor Inhibitor: A Report of Three Cases," Oncol. Res., 15:107-111 (2005).
Yu et al., "The proteasome inhibitor bortezpmib interacts synergistically with histone deacetylase inhibitors to induce apoptosis in Bcr/Abl+ cells sensitive and resistant to STI571," Blood, 102(10):3765-3774 (2003).
Zhang et al., "Histone deacetylase inhibitor romidepsin enhances anti-tumor effect of erlotinib in non-small cell lung cancer (NSCLC) cell lines," Journal of Throacic Oncocology, 4(2): 161-166 (2009).
Non final office action dated Jun. 8, 2011 in U.S. Appl. No. 12/298,436.
Final office action dated Feb. 1, 2012 in U.S. Appl. No. 12/298,436.
Non final office action dated Jul. 12, 2013 in U.S. Appl. No. 13/229,581.
Non final office action dated Oct. 17, 2013 in U.S. Appl. No. 13/627,848.
Final office action dated Apr. 2, 2014 in U.S Appl. No. 13/627,848.

* cited by examiner

INHIBITION OF DRUG RESISTANT CANCER CELLS

This application claims the benefit of priority of U.S. provisional application Ser. No. 61/726,502, filed Nov. 14, 2012, U.S. provisional application Ser. No. 61/793,638, filed Mar. 15, 2013, and U.S. provisional application Ser. No. 61/805,852, filed Mar. 27, 2013, each of which is incorporated herein by reference in its entirety.

FIELD

Provided are methods for inhibiting or preventing the growth of drug resistant cancer cells using histone deacetylase (HDAC) inhibitors. In one embodiment, the HDAC inhibitor is romidepsin.

BACKGROUND

Resistance to anticancer drugs represents a major obstacle to successful cancer treatment. Various resistance mechanisms and alternate survival pathways have been described (Redmond et al., *Front Biosci* 13:5138-5154, 2008). Recent findings have revealed non-mutational mechanisms of drug resistance. Trumpp and Wiesletler (*Nat Clin Prac Oncol* 5, 337-347, 2008) described a small population of "cancer stem cells" that are intrinsically more refractory to the effects of a variety of anticancer drugs, possibly via enhanced drug efflux. Other studies have implicated epigenetic mechanisms, suggesting that acquired drug resistance does not necessarily require a stable heritable genetic alteration (Glasspool et al., *Br J Cancer*, 94:1087-1092, 2006). It was demonstrated in non-small cell lung cancer (NSCLC) patients, who responded well to treatment with epidermal growth factor receptor (EGFR) tyrosine kinase inhibitors (TKIs), and who later experienced therapy failure, but demonstrated a second response to EGFR TKI re-treatment after a "drug holiday" (Kurata et al., *Ann Oncol* 15:173-174, 2004; Yano et al., *Oncol Res* 15:107-111, 2005). Similar re-treatment responses are well established for several other anticancer drugs (Cara & Tannock, *Ann Oncol* 12:23-37, 2001). These findings suggest that acquired resistance to cancer drugs involves a reversible "drug-tolerant" state.

Recent data point to the pre-existence of a subpopulation of cancer cells termed drug-tolerant persisters (DTPs) that exhibit an epigenetically-mediated tolerance to high concentrations of chemotherapeutic drugs (Sharma et al., *Cell* 141:69-80, 2010). Although DTPs are largely quiescent, a small fraction of these cells resumes growth even in the presence of 100×IC$_{50}$ drug concentrations, giving rise to drug-tolerant expanded persisters (DTEPs). Levels of histone H3 lysine 4 (H3K4) methylation and H3K14 acetylation are significantly decreased in DTPs and DTEPs.

As resistance to anticancer drugs remains a major challenge in anticancer therapy, there is a need for compounds capable to overcome this resistance.

SUMMARY

In one embodiment, provided herein are methods of treating cancer in a cancer patient by overcoming resistance of a cancer cell to a drug, comprising administering to the patient an effective amount of (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are administered simultaneously. In another embodiment, the HDAC inhibitor is administered after pretreatment with the EGFR tyrosine kinase inhibitor or the B-Raf kinase inhibitor.

In another embodiment, provided herein are methods for overcoming drug-resistance of a cancer cell in a patient, comprising administering to the patient an effective amount of (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are administered simultaneously. In another embodiment, the HDAC inhibitor is administered after pretreatment with the EGFR tyrosine kinase inhibitor or the B-Raf kinase inhibitor.

HDAC inhibitors for use in methods provided herein include, but are not limited to, trichostatin A (TSA), Vorinostat (SAHA), Valproic Acid (VPA), romidepsin and MS-275. In one embodiment, the HDAC inhibitor is romidepsin.

In another embodiment, the drug is a EGFR tyrosine kinase inhibitor. EGFR tyrosine kinase inhibitors suitable for use in the methods provided herein include, but are not limited to, Erlotinib, Getifinib, Lapatinib, Afatinib, Canertinib, Neratinib, Pelitinib, CP-724714, CUDC-101, and WZ4002. In one embodiment, the EGFR tyrosine kinase inhibitor is Erlotinib.

In yet another embodiment, the drug is a B-Raf kinase inhibitor. B-Raf kinase inhibitors suitable for use in the methods provided herein include, but are not limited to, Vemurafenib (PLX4032), Sorafenib (AZ628), Dabrafenib, PLX4720, GDC-0879, RAF-265, and SB690885. In one embodiment, the B-Raf kinase inhibitor is Vemurafenib. In another embodiment, the B-Raf kinase inhibitor is Sorafenib.

In one embodiment, cancers that can be treated by the methods provided herein are solid tumors. In one embodiment, the cancer is a skin cancer. In another embodiment, the cancer is a lung cancer.

In one embodiment, provided herein are methods for inhibiting or preventing proliferation of drug-tolerant persisters (DTP) resistant to EGFR tyrosine kinase inhibitors or serine/threonine protein kinase B-Raf (B-Raf) kinase inhibitors, comprising contacting the DTPs with (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are added to the cancer cells simultaneously. In another embodiment, the cancer cells are treated with the HDAC inhibitor after contacting with EGFR tyrosine kinase inhibitor or the B-Raf kinase inhibitor.

In one embodiment, provided herein are methods for inhibiting or preventing formation of colonies of drug-tolerant expanded persisters (DTEP) resistant to EGFR tyrosine kinase inhibitors or B-RAF kinase inhibitors, comprising contacting the DTEPs with (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are added to the cancer cells simultaneously. In another embodiment, the cancer cells are treated with the HDAC inhibitor after contacting with EGFR tyrosine kinase inhibitor or the B-Raf kinase inhibitor.

In one embodiment, EGFR tyrosine kinase inhibitor is any EGFR tyrosine kinase inhibitor. EGFR tyrosine kinase inhibitors suitable for use in the methods provided herein include, but are not limited to, Erlotinib, Getifinib, Lapatinib, Afatinib, Canertinib, Neratinib, Pelitinib, CP-724714, CUDC-101, and WZ4002. In one embodiment, the EGFR tyrosine kinase inhibitor is Erlotinib.

In one embodiment, B-Raf kinase inhibitor is any B-Raf kinase inhibitor. B-Raf kinase inhibitors suitable for use in the methods provided herein include, but are not limited to, Vemurafenib (PLX4032), Sorafenib (AZ628), Dabrafenib, PLX4720, GDC-0879, RAF-265, and SB690885. In one embodiment, the B-Raf kinase inhibitor is Vemurafenib. In another embodiment, the B-Raf kinase inhibitor is Sorafenib.

HDAC inhibitors for use in methods provided herein include, but are not limited to, trichostatin A (TSA), Vorinostat (SAHA), Valproic Acid (VPA), romidepsin and MS-275. In one embodiment, the HDAC inhibitor is romidepsin.

In one embodiment, provided herein is a pharmaceutical composition for treating a drug resistant cancer in a patient In one embodiment, the pharmaceutical composition comprises (i) an EGFR tyrosine kinase inhibitor or a B-Raf kinase inhibitor, and (ii) an HDAC inhibitor. In one embodiment, the HDAC inhibitor is romidepsin. In another embodiment, the EGFR tyrosine kinase inhibitor is Erlotinib. In yet another embodiment, the B-Raf kinase inhibitor is Vemurafenib. In yet another embodiment, the B-Raf kinase inhibitor is Sorafenib.

The present embodiments can be understood more fully by reference to the detailed description and examples, which are intended to exemplify non-limiting embodiments.

DETAILED DESCRIPTION

Definitions

Figure 1:
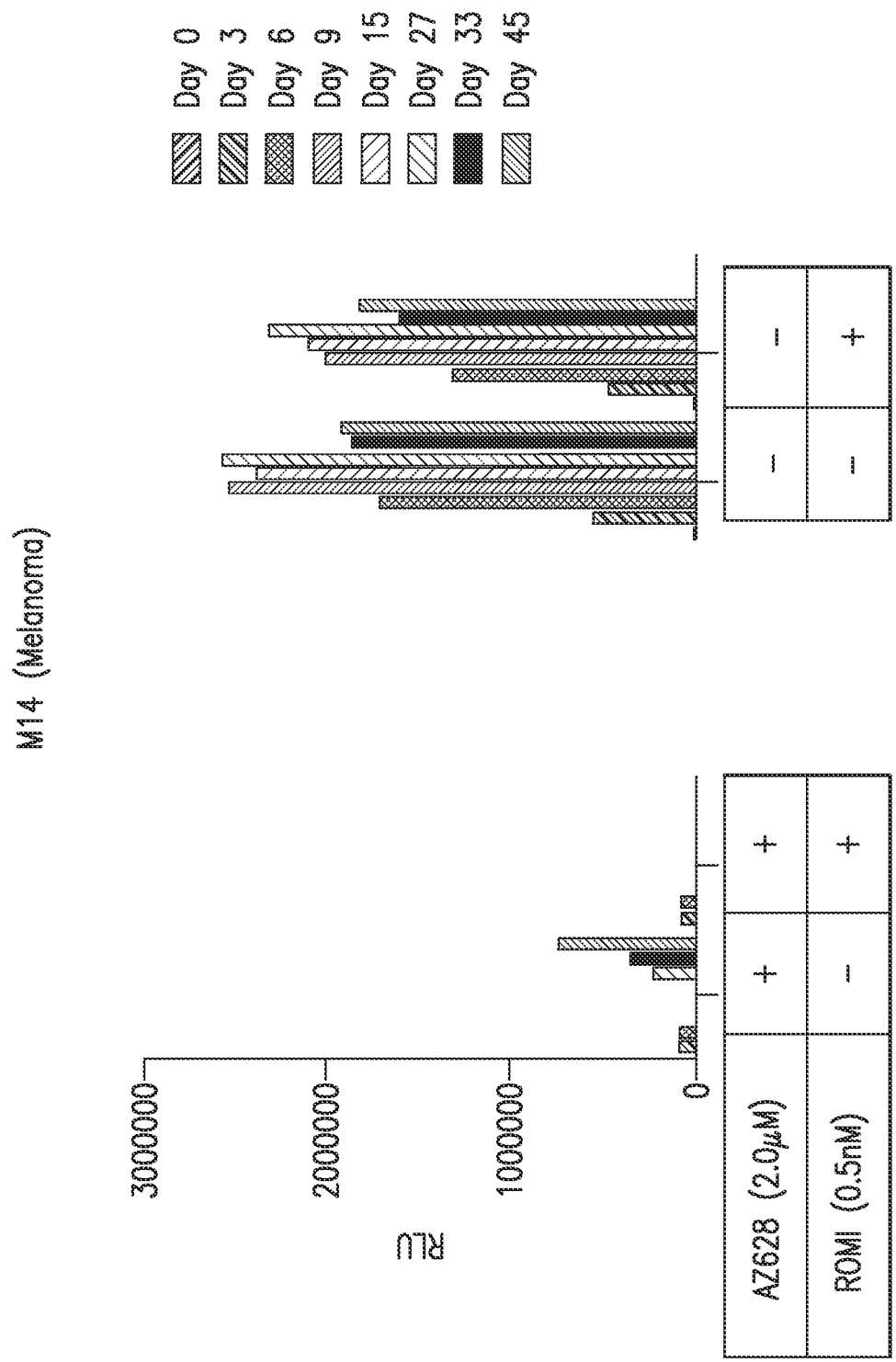
FIG. 1 shows the effect of the combination of AZ628 and romidepsin on DTEP emergence in a melanoma cell line (M14). Both agents were added to the cells every 3 days during the "continuous" schedule (45 days) at a concentration of 2 µM for AZ628 and 0.5 nM for romidepsin. Cell viability was measured on select days using CellTiter-Glo.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. It should also be noted that use of "or" means "and/or" unless stated otherwise. Furthermore, use of the term "including" as well as other forms, such as "include," "includes," and "included" is not limiting.

The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus.

The term "proliferative disorder or disease" as used herein refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders The term "proliferation" as used herein refers to a rapid and repeated succession of divisions of cells, e.g., cancer cells.

The term "chemoresistant cancer" as used herein means a type of cancer that has been responding to a therapy then begins to grow because the cancer cells are not responsive to the effects of chemotherapy.

The term "melanoma" as used herein means a malignant tumor of melanocytes. Melanoma originates in the skin where melanocytes predominantly occur but can originate in any part of the body that contains melanocytes.

The term "non-small cell lung cancer" as used herein refers to any type of epithelial lung cancer other than small cell lung cancer.

The term "treating" as used herein, means an alleviation, in whole or in part, of symptoms associated with a disorder or disease (e.g., cancer or a tumor syndrome), or slowing, or halting of further progression or worsening of those symptoms.

The term "inhibiting" as used herein, means slowing or reducing the growth of a cell or a cell line (e.g., cancer cell or cancer cell line).

The term "preventing" as used herein, means the absence or lack of growth of a cell or a cell line (e.g., cancer cell or cancer cell line).

The term "emergence" as used herein, means occurrence or recurrence of drug resistant cancer cells in a cancer cell population.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "drug-tolerant persisters (DTPs)" as used herein, refers to cancer cells that have a tolerance to high concentrations of chemotherapeutic drugs i.e. that are resistant to a cancer drug treatment, when the drug used in concentrations that are hundreds of times higher than $IC_{50}$.

The term "drug-tolerant expanded persisters (DTEPs)" as used herein, refers to cancer cells that are capable to proliferate with continuous cancer drug treatment in high concentrations.

The term "cancer cell" as used herein, refers to a cell of any origin that grows and divides at an unregulated, quickened pace.

The term "cancer cell line" as used herein, refers to a line of cells established from a primary cancer cell, in which all cells possess the same properties.

The terms "drug," "therapeutic agent," and "chemotherapeutic agent" as used herein refer to a compound, or a pharmaceutical composition thereof, which is administered to a subject for treating, preventing, or ameliorating one or more symptoms of a condition, disorder, or disease.

The term "epidermal growth factor receptor (EGFR)" as used herein, refers to the cell-surface receptor for members of the epidermal growth factor family (EGF-family).

The term "tyrosine kinase" as used herein, refers to enzymes responsible for the activation of signal transduction cascades via phosphorylation of tyrosine hydroxyl moieties in substrate proteins.

The term "tyrosine kinase inhibitors" as used herein, refers to a chemical compound such as a pharmaceutical drug that inhibits tyrosine kinases.

The term "effective amount" in connection with the HDAC inhibitor means an amount capable of alleviating, in whole or in part, symptoms associated with a disorder, for example cancer, or slowing or halting further progression or worsening of those symptoms, or preventing or providing prophylaxis for cancer, in a subject at risk for cancer. The effective amount of the HDAC inhibitor, for example in a pharmaceutical composition, may be at a level that will exercise the desired effect; for example, about 0.005 mg/kg of a subject's body weight to about 100 mg/kg of a subject's body weight in unit dosage for both oral and parenteral administration. As will be apparent to those skilled in the art, it is to be expected that the effective amount of an HDAC inhibitor disclosed herein may vary depending on the severity of the indication being treated.

As used herein, and unless otherwise specified, the term "in combination with" includes the administration of two or more therapeutic agents simultaneously, concurrently, or sequentially within no specific time limits unless otherwise indicated. In one embodiment, an HDAC inhibitor is administered in combination with a EGFR tyrosine kinase inhibitor or a B-Raf kinase inhibitor. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, or any combination thereof. For example, in one embodiment, the first agent can be administered prior to the second therapeutic agent, for e.g. 1 week. In another, the first agent can be administered prior to (for example 1 day prior) and then concomitant with the second therapeutic agent.

The term "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from the administration site of one organ, or portion of the body, to another organ, or portion of the body, or in an in vitro assay system. Each carrier must be "acceptable" in the sense of being compatible with the other ingredients of the formulation and not injurious to a subject to whom it is administered. Nor should an acceptable carrier alter the specific activity of the subject compounds.

The term "pharmaceutically acceptable" refers to molecular entities and compositions that are physiologically tolerable and do not typically produce an allergic or similar untoward reaction, such as gastric upset, dizziness and the like, when administered to a human.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein.

The term "dosage form" as used herein refers to physically discrete units suitable as unitary dosage for humans, each unit containing a predetermined quantity of active material calculated to produce the desired therapeutic effect in association with the required diluent; i.e., carrier, or vehicle. In one embodiment, the active ingredient is romidepsin.

The term "unit dosage form" as used herein means a physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. A unit-dosage form may be administered in fractions or multiples thereof. Examples of a unit-dosage form include an ampoule, syringe, and individually packaged tablet and capsule.

The term "multiple-dosage form" as used herein refers to a plurality of identical unit-dosage forms packaged in a single container to be administered in segregated unit-dosage form. Examples of a multiple-dosage form include a vial, bottle of tablets or capsules, or bottle of pints or gallons.

The term "biological sample" is intended to include tissues (including, but are not limited to, tissue biopsies), cells, biological fluids and isolates thereof, isolated from a subject, as well as tissues, cells and fluids present within a subject.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Romidepsin

Romidepsin is a natural product which was isolated from *Chromobacterium violaceum* by Fujisawa Pharmaceuticals (Published Japanese Patent Application No. 64872, U.S. Pat. No. 4,977,138, issued Dec. 11, 1990, Ueda et al., *J. Antibiot* (Tokyo) 47:301-310, 1994; Nakajima et al., *Exp Cell Res* 241:126-133, 1998; and WO 02/20817; each of which is incorporated herein by reference. It is a bicyclic peptide consisting of four amino acid residues (D-valine, D-cysteine, dehydrobutyrine, and L-valine) and a novel acid (3-hydroxy-7-mercapto-4-heptenoic acid) containing both amide and ester bonds. In addition to the production from *C. violaceum* using fermentation, romidepsin can also be prepared by synthetic or semi-synthetic means. The total synthesis of romidepsin reported by Kahn et al. involves 14 steps and yields romidepsin in 18% overall yield (Kahn et al. *J. Am. Chem. Soc.* 118:7237-7238, 1996).

The chemical name of romidepsin is (1S,4S,7Z,10S,16E, 21R)-7-ethylidene-4,21-bis(1-methylethyl)-2-oxa-12,13-dithia-5,8,20,23-tetrazabicyclo[8.7.6]tricos-16-ene-3,6,9, 19,22-pentone. The empirical formula is $C_{24}H_{36}N_4O_6S_2$. The molecular weight is 540.71. At room temperature, romidepsin is a white powder.

It's structure is shown below (formula I):

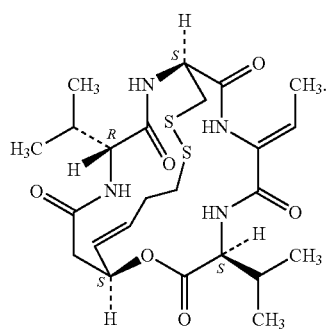

(I)

Romidepsin has been shown to have anti-microbial, immunosuppressive, and anti-tumor activities. It was tested, for example, for use in treating patients with hematological malignancies (e.g, cutaneous T-cell lymphoma (CTCL), peripheral T-cell lymphoma (PTCL), multiple myeloma, etc.) and solid tumors (e.g., prostate cancer, pancreatic cancer, etc.) and is thought to act by selectively inhibiting deacetylases (e.g., histone deacetylase, tubulin deacetylase), thus promising new targets for the development of a new class of anti-cancer therapies (Nakajima et al., *Exp Cell Res* 241:126-133, 1998). One mode of action of romidepsin involves the inhibition of one or more classes of histone deacetylases (HDAC). Preparations and purification of romidepsin is described, for example, in U.S. Pat. No. 4,977,138 and International PCT Application Publication WO 02/20817, each of which is incorporated herein by reference.

Exemplary forms of romidepsin include, but are not limited to, salts, esters, pro-drugs, isomers, stereoisomers (e.g., enantiomers, diastereomers), tautomers, protected forms, reduced forms, oxidized forms, derivatives, and combinations thereof, with the desired activity (e.g., deacetylase inhibitory activity, aggressive inhibition, cytotoxicity). In certain embodiments, romidepsin is a pharmaceutical grade material and meets the standards of the U.S. Pharmacopoeia, Japanese Pharmacopoeia, or European Pharmacopoeia. In certain embodiments, the romidepsin is at least 95%, at least 98%, at least 99%, at least 99.9%, or at least 99.95% pure. In certain embodiments, the romidepsin is at least 95%, at least 98%, at least 99%, at least 99.9%, or at least 99.95% monomeric. In certain embodiments, no impurities are detectable in the romidepsin materials (e.g., oxidized material, reduced material, dimerized or oligomerized material, side products, etc.). Romidepsin typically includes less than 1.0%, less than 0.5%, less than 0.2%, or less than 0.1% of total other unknowns. The purity of romidepsin may be assessed by appearance, HPLC, specific rotation, NMR spectroscopy, IR spectroscopy, UV/Visible spectroscopy, powder x-ray diffraction (XRPD) analysis, elemental analysis, LC-mass spectroscopy, or mass spectroscopy.

In one embodiment, romidepsin is a derivative of romidepsin of the formula (II):

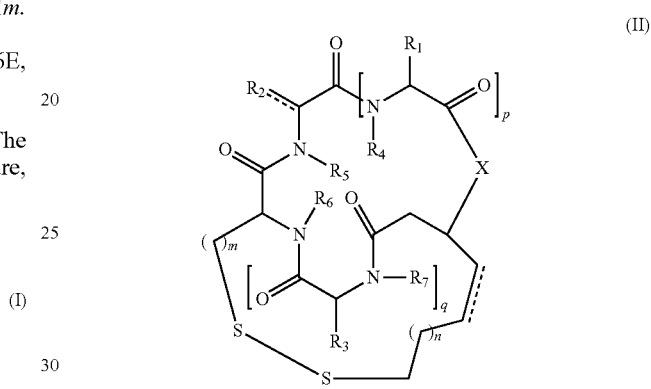

(II)

wherein
n is 1, 2, 3 or 4;
n is 0, 1, 2 or 3;
p and q are independently 1 or 2;
X is 0, NH, or $NR_8$;
$R_1$, $R_2$, and $R_3$ are independently hydrogen, unsubstituted or substituted, branched or unbranched, cyclic or acyclic aliphatic; unsubstituted or substituted, branched or unbranched, cyclic or acyclic heteroaliphatic; unsubstituted or substituted aryl; or unsubstituted or substituted heteroaryl; and $R_4$, $R_5$, $R_6$, $R_7$ and $R_8$ are independently hydrogen, or substituted or unsubstituted, branched or unbranched, cyclic or acyclic aliphatic; and pharmaceutically acceptable forms thereof.

In one embodiment, m is 1, n is 1, p is 1, q is 1, X is 0, $R_1$, $R_2$, and $R_3$ are unsubstituted or substituted, branched or unbranched acyclic aliphatic. In one embodiment, $R_4$, $R_5$, $R_6$ and $R_7$ are all hydrogen.

In one embodiment, the derivative of romidepsin is of the formula (III):

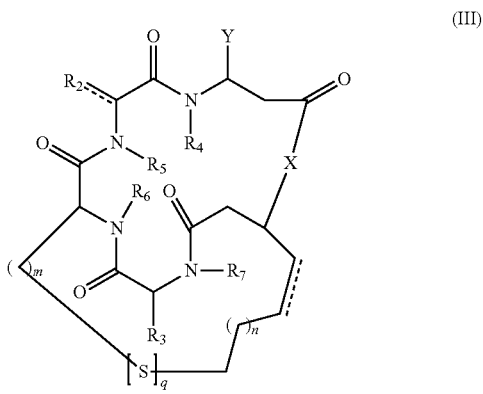

(III)

wherein:
  m is 1, 2, 3 or 4;
  n is 0, 1, 2 or 3;
  q is 2 or 3;
  X is O, NH, or $NR_8$;
  Y is ORB, or $SR_8$;
  $R_2$ and $R_3$ are independently hydrogen, unsubstituted or substituted, branched or unbranched, cyclic or acyclic aliphatic, unsubstituted or substituted, branched or unbranched, cyclic or acylic heteroaliphatic, unsubstituted or substituted aryl or unsubstituted or substituted heteroaryl;
  $R_4$, $R_5$, $R_6$, $R_7$ and $R_8$ are independently selected from hydrogen or substituted or unsubstituted, branched or unbranched, cyclic or acyclic aliphatic, and pharmaceutically acceptable forms thereof.
  In one embodiment, m is 1, n is 1, q is 2, X is NH and $R_2$ and $R_3$ are unsubstituted or substituted, branched or unbranched, acyclic aliphatic. In one embodiment, $R_4$, $R_5$, $R_6$ and $R_7$ are all hydrogen.
  In one embodiment, the derivative of romidepsin is of the formula (IV):

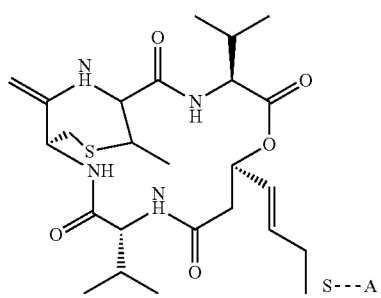

(IV)

wherein:
  A is a moiety that is cleaved under physiological conditions to yield a thiol group and includes, for example, an aliphatic or aromatic acyl moiety (to form a thioester bond), an aliphatic or aromatic thioxy (to form a disulfide bond), or the like, and pharmaceutically acceptable forms thereof. Such aliphatic or aromatic groups can include a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group. A can be, for example, —$COR_1$, —SC(=O)—O—$R_1$, or —$SR_2$;
  $R_1$ is independently hydrogen, substituted or unsubstituted amino, substituted or unsubstituted, branched or unbranched, cyclic or acyclic aliphatic, substituted or unsubstituted aromatic group, substituted or unsubstituted heteroaromatic group, or a substituted or unsubstituted heterocyclic group. In one embodiment, $R_1$ is hydrogen, methyl, ethyl, n-propyl, isopropyl, n-butyl, isobutyl, benzyl, or bromobenzyl;
  $R_2$ is a substituted or unsubstituted, branched or unbranched, cyclic or acyclic aliphatic group, a substituted or unsubstituted aromatic group, a substituted or unsubstituted heteroaromatic group, or a substituted or unsubstituted heterocyclic group.
  In one embodiment, $R_2$ is methyl, ethyl, 2-hydroxyethyl, isobutyl, a fatty acid, a substituted or unsubstituted benzyl, a substituted or unsubstituted aryl, cysteine, homocysteine, or glutathione.
  In one embodiment, the derivative of romidepsin is of formula (V) or (V'):

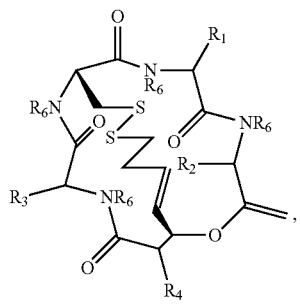

(V)

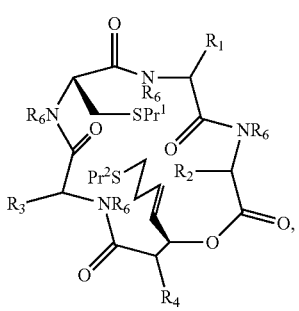

(V')

wherein
  each of $R_1$, $R_2$, $R_3$ and $R_4$ is the same or different and represent an amino acid side chain moiety;
  each $R_6$ is the same or different and represents hydrogen or ($C_1$-$C_4$)alkyl; and
  $Pr^1$ and $Pr^2$ are the same or different and represent hydrogen or thiol-protecting group.
  In one embodiment, the amino acid side chain moieties are those derived from natural amino acids. In one embodiment, the amino acid side chain moieties are those derived from unnatural amino acids.
  In one embodiment, each amino acid side chain is a moiety selected from hydrogen, ($C_1$-$C_6$)alkyl, ($C_2$-$C_6$)alkenyl, -L-O—C(O)-R', -L-C(O)—O—R", -L-A, -L-NR"R", -L-Het-C(O)-Het-R", and -L-Het-R", wherein L is a ($C_1$-$C_6$)alkylene group, A is phenyl or a 5- or 6-membered heteroaryl group, each R' is the same or different and represents ($C_1$-$C_4$)alkyl, each R" is the same or different and represent H or ($C_1$-$C_6$) alkyl, each -Het- is the same or different and is a heteroatom spacer selected from —O—, —N(R''')—, and —S—, and each R''' is the same of different and represents hydrogen or ($C_1$-$C_4$)alkyl.
  In one embodiment, $R_6$ is hydrogen.
  In one embodiment, $Pr^1$ and $Pr^2$ are the same or different and are selected from hydrogen and a protecting group selected from a benzyl group which is optionally substituted by ($C_1$-$C_6$)alkoxy, ($C_1$-$C_6$)acyloxy, hydroxy, nitro, picolyl, picolyl-N-oxide, anthrylmethyl, diphenylmethyl, phenyl, t-butyl, adamanthyl, ($C_1$-$C_6$)acyloxymethyl, ($C_1$-$C_6$) alkoxymethyl, tetrahydropyranyl, benzylthiomethyl, phenylthiomethyl, thiazolidine, acetamidemethyl, benzamidomethyl, tertiary butoxycarbonyl (BOC), acetyl and its derivatives, benzoyl and its derivatives, carbamoyl, phenylcarbamoyl, and ($C_1$-$C_6$)alkylcarbamoyl. In one embodiment, $Pr^1$ and $Pr^2$ are hydrogen.
  Various romidepsin derivatives of formula (V) and (V') are disclosed in PCT application publication WO 2006/129105, published Dec. 7, 2006, which is incorporated herein by reference.

Methods of Use

In one embodiment, provided herein are methods of treating cancer in a cancer patient by overcoming resistance of a cancer cell to a drug, comprising administering to the patient an effective amount of (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are administered simultaneously. In another embodiment, the HDAC inhibitor is administered after pretreatment with the EGFR tyrosine kinase inhibitor or the B-Raf kinase inhibitor.

In another embodiment, provided herein are methods for overcoming drug-resistance of a cancer cell in a patient, comprising administering to the patient an effective amount of (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are administered simultaneously. In another embodiment, the HDAC inhibitor is administered after pretreatment with the EGFR tyrosine kinase inhibitor or the B-Raf kinase inhibitor.

HDAC inhibitors for use in methods provided herein include, but are not limited to, trichostatin A (TSA), Vorinostat (SAHA), Valproic Acid (VPA), romidepsin and MS-275. In one embodiment, the HDAC inhibitor is romidepsin.

In another embodiment, the drug is a EGFR tyrosine kinase inhibitor. EGFR tyrosine kinase inhibitors suitable for use in the methods provided herein include, but are not limited to, Erlotinib, Getifinib, Lapatinib, Afatinib, Canertinib, Neratinib, Pelitinib, CP-724714, CUDC-101, and WZ4002. In one embodiment, the EGFR tyrosine kinase inhibitor is Erlotinib.

In yet another embodiment, the drug is a B-Raf kinase inhibitor. B-Raf kinase inhibitors suitable for use in the methods provided herein include, but are not limited to, Vemurafenib (PLX4032), Sorafenib (AZ628), Dabrafenib, PLX4720, GDC-0879, RAF-265, and SB690885. In one embodiment, the B-Raf kinase inhibitor is Vemurafenib. In another embodiment, the B-Raf kinase inhibitor is Sorafenib.

In one embodiment, cancers that can be treated by the methods provided herein are solid tumors. In some such embodiments the disclosure relates to treatment of solid tumors such as lung, skin, breast, colon, liver, pancreas, renal, prostate, ovarian, and/or brain. In some embodiments, the disclosure relates to treatment of a lung cancer. In some embodiments, the disclosure relates to treatment of a skin cancer.

In one embodiment, the skin cancer that can be treated by the methods provided herein is melanoma. In one embodiment, the lung cancer that can be treated by the methods provided herein is a non-small cell lung cancer.

An HDAC inhibitor may be administered using different routes of administration including, but not limited to, oral, rectal, transmucosal, transdermal, intestinal, and parenteral. In one embodiment, the HDAC inhibitor is romidepsin.

In one embodiment, romidepsin is administered intravenously. In one embodiment, romidepsin is administered intravenously over a time period less than about 1 hour. In one embodiment, romidepsin is administered intravenously over a 1-6 hour period. In one embodiment, romidepsin is administered intravenously over a 3-4 hour period. In one embodiment, romidepsin is administered intravenously over a 5-6 hour period. In one embodiment, romidepsin is administered intravenously over a 4 hour period.

In one embodiment, romidepsin is administered intravenously in a dose ranging from 0.5 mg/m$^2$ to 28 mg/m$^2$. In one embodiment, romidepsin is administered in a dose ranging from 0.5 mg/m$^2$ to 5 mg/m$^2$. In one embodiment, romidepsin is administered in a dose ranging from 1 mg/m$^2$ to 25 mg/m$^2$. In one embodiment, romidepsin is administered in a dose ranging from 1 mg/m$^2$ to 20 mg/m$^2$. In one embodiment, romidepsin is administered in a dose ranging from 1 mg/m$^2$ to 15 mg/m$^2$. In one embodiment, romidepsin is administered in a dose ranging from 2 mg/m$^2$ to 15 mg/m$^2$. In one embodiment, romidepsin is administered in a dose ranging from 2 mg/m$^2$ to 12 mg/m$^2$. In one embodiment, romidepsin is administered in a dose ranging from 4 mg/m$^2$ to 12 mg/m$^2$. In one embodiment, romidepsin is administered in a dose ranging from 6 mg/m$^2$ to 12 mg/m$^2$. In one embodiment, romidepsin is administered in a dose ranging from 8 mg/m$^2$ to 12 mg/m$^2$. In one embodiment, romidepsin is administered in a dose ranging from 8 mg/m$^2$ to 10 mg/m$^2$. In one embodiment, romidepsin is administered in a dose of about 8 mg/m$^2$. In one embodiment, romidepsin is administered in a dose of about 9 mg/m$^2$. In one embodiment, romidepsin is administered in a dose of about 10 mg/m$^2$. In one embodiment, romidepsin is administered in a dose of about 11 mg/m$^2$. In one embodiment, romidepsin is administered in a dose of about 12 mg/m$^2$. In one embodiment, romidepsin is administered in a dose of about 13 mg/m$^2$. In one embodiment, romidepsin is administered in a dose of about 14 mg/m$^2$. In one embodiment, romidepsin is administered in a dose of about 15 mg/m$^2$.

In one embodiment, romidepsin is administered in a dose of 14 mg/m$^2$ as an IV infusion over a 4 hour period on days 1, 8 and 15 of the 28 day cycle. In one embodiment, the cycle is repeated every 28 days.

In one embodiment, increasing doses of romidepsin are administered over the course of a cycle. In one embodiment, the dose of about 8 mg/m$^2$ followed by a dose of about 10 mg/m$^2$, followed by a dose of about 12 mg/m$^2$ is administered over a cycle.

In one embodiment, romidepsin is administered intravenously in a dose ranging from 0.05 mg/m$^2$ to 5 mg/m$^2$. In one embodiment, romidepsin is administered in a dose ranging from 0.1 mg/m$^2$ to 4 mg/m$^2$. In one embodiment, romidepsin is administered in a dose ranging from 0.5 mg/m$^2$ to 2.5 mg/m$^2$. In one embodiment, romidepsin is administered in a dose ranging from 1 mg/m$^2$ to 2 mg/m$^2$. In one embodiment, romidepsin is administered in a dose of about 0.1 mg/m$^2$. In one embodiment, romidepsin is administered in a dose of about 0.5 mg/m$^2$. In one embodiment, romidepsin is administered in a dose of about 1.0 mg/m$^2$. In one embodiment, romidepsin is administered in a dose of about 2.0 mg/m$^2$. In one embodiment, romidepsin is administered in a dose of about 3.0 mg/m$^2$. In one embodiment, romidepsin is administered in a dose of about 4.0 mg/m$^2$. In one embodiment, romidepsin is administered in a dose of about 5.0 mg/m$^2$.

In one embodiment, romidepsin is administered in a dose of 0.5 mg/m$^2$ over a 4 hour iv infusion on days 1, 8 and 15 of the 28 day cycle. In one embodiment, romidepsin is administered in a dose of 1.0 mg/m$^2$ over a 4 hour iv infusion on days 1, 8 and 15 of the 28 day cycle. In one embodiment, romidepsin is administered in a dose of 2.0 mg/m$^2$ over a 4 hour iv infusion on days 1, 8 and 15 of the 28 day cycle. In one embodiment, romidepsin is administered in a dose of 3.0 mg/m$^2$ over a 4 hour iv infusion on days 1, 8 and 15 of the 28 day cycle. In one embodiment, romidepsin is administered in a dose of 4.0 mg/m$^2$ over a 4 hour iv infusion on days 1, 8 and 15 of the 28 day cycle. In one embodiment, romidepsin is administered in a dose of 5.0 mg/m$^2$ over a 4 hour iv infusion on days 1, 8 and 15 of the 28 day cycle. In one embodiment, the cycle is repeated every 28 days.

In one embodiment, increasing doses of an HDAC inhibitor are administered over the course of a cycle. In one embodiment, the dose of about 1.0 mg/m² followed by a dose of about 3.0 mg/m², followed by a dose of about 5.0 mg/m² is administered over a cycle.

In one embodiment, romidepsin is administered orally. In one embodiment, romidepsin is administered in a dose ranging from 0.1 mg/m² to 10 mg/m². In one embodiment, romidepsin is administered in a dose ranging from 0.5 mg/m² to 5.0 mg/m². In one embodiment, romidepsin is administered in a dose ranging from 1.0 mg/m² to 4.0 mg/m². In one embodiment, romidepsin is administered in a dose ranging from 2.5 mg/m² to 3.5 mg/m².

In another embodiment, romidepsin is administered orally in a dose ranging from 10 mg/m² to 300 mg/m². In one embodiment, romideepsin is administered in a dose ranging from 15 mg/m² to 250 mg/m². In one embodiment, romidepsin is administered in a dose ranging from 20 mg/m² to 200 mg/m². In one embodiment, romidepsin is administered in a dose ranging from 25 mg/m² to 150 mg/m². In one embodiment, romidepsin is administered in a dose ranging from 25 mg/m² to 100 mg/m². In one embodiment, romidepsin is administered in a dose ranging from 25 mg/m² to 75 mg/m².

In one embodiment, romidepsin is administered orally on a daily basis. In certain embodiments, romidepsin is dosed orally in the range of 10 mg/m² to 300 mg/m². In certain embodiments, romidepsin is dosed orally in the range of 25 mg/m² to 100 mg/m². In certain embodiments, romidepsin is dosed orally in the range of 100 mg/m² to 200 mg/m². In certain embodiments, romidepsin is dosed orally in the range of 200 mg/m² to 300 mg/m². In certain embodiments, romidepsin is dosed orally at greater than 300 mg/m². In certain embodiments, romidepsin is dosed orally in the range of 50 mg/m² to 150 mg/m². In other embodiments, the oral dosage ranges from 25 mg/m² to 75 mg/m². In one embodiment, romidepsin is administered orally every other day. In one embodiment, romidepsin is administered orally every third, fourth, fifth, or sixth day. In one embodiment, romidepsin is administered orally every week. In one embodiment, romidepsin is administered orally every other week.

In one embodiment, romidepsin is administered orally in a dose of 50 mg/m² on days 1, 8 and 15 of the 28 day cycle. In one embodiment, the cycle is repeated every 28 days.

In one embodiment, increasing doses of romidepsin are administered over the course of a cycle. In one embodiment, the dose of about 25 mg/m² followed by a dose of about 50 mg/m², followed by a dose of about 75 mg/m² is administered over a cycle.

In one embodiment, one cycle comprises the administration of from about 25 to about 150 mg/m² of romidepsin daily for three to four weeks and then one or two weeks of rest. In one embodiment, the number of cycles during which the treatment is administered to a patient will be from about one to about 40 cycles, or from about one to about 24 cycles, or from about two to about 16 cycles, or from about four to about three cycles.

In one embodiment, romidepsin is administered to a cancer patient in combination with an EGFR tyrosine kinase inhibitor. An EGFR tyrosine kinase inhibitor may be administered using different routes of administration including, but not limited to, oral, rectal, transmucosal, transdermal, intestinal, and parenteral. In one embodiment, the EGFR tyrosine kinase inhibitor is Erlotinib.

In one embodiment, Erlotinib is administered orally. In one embodiment, Erlotinib is administered in a dose ranging from 1 mg/day to 500 mg/day. In one embodiment, Erlotinib is administered in a dose ranging from 10 mg/day to 450 mg/day. In one embodiment, Erlotinib is administered in a dose ranging from 25 mg/day to 250 mg/day. In one embodiment, Erlotinib is administered in a dose ranging from 50 mg/day to 150 mg/day. In one embodiment, Erlotinib is administered in a dose of 25 mg/day. In one embodiment, Erlotinib is administered in a dose of 50 mg/day. In one embodiment, Erlotinib is administered in a dose of 75 mg/day. In one embodiment, Erlotinib is administered in a dose of 100 mg/day. In one embodiment, Erlotinib is administered in a dose of 125 mg/day. In one embodiment, Erlotinib is administered in a dose of 150 mg/day.

In one embodiment, the dose of romidepsin is about 0.05 mg/m² to 5 mg/m² and the dose of Erlotinib is about 25 mg/day to about 250 mg/day. In another embodiment, the dose of romidepsin is about 0.5 mg/m² to 2.5 mg/m² and the dose of Erlotinib is about 50 mg/day to about 150 mg/day. In yet another embodiment, the dose of romidepsin is about 2.5 mg/m² and the dose of Erlotinib is about 150 mg/day. In one embodiment, romidepsin and Erlotinib are administered to the cancer patient simultaneously. In another embodiment, romidepsin is administered to the cancer patient after the patient was pretreated with Erlotinib. In one embodiment, the cancer patient is a non-small cell lung cancer patient.

In another embodiment, the dose of romidepsin is about 5 mg/m² to 15 mg/m² and the dose of Erlotinib is about 25 mg/day to about 250 mg/day. In another embodiment, the dose of romidepsin is about 8 mg/m² to 12 mg/m² and the dose of Erlotinib is about 50 mg/day to about 150 mg/day. In yet another embodiment, the dose of romidepsin is about 10 mg/m² and the dose of Erlotinib is about 150 mg/day. In one embodiment, romidepsin and Erlotinib are administered to the cancer patient simultaneously. In another embodiment, romidepsin is administered to the cancer patient after the patient was pretreated with Erlotinib. In one embodiment, the cancer patient is a non-small cell lung cancer patient.

In one embodiment, romidepsin is administered to a cancer patient in combination with a B-Raf kinase inhibitor. The B-Raf kinase inhibitor may be administered using different routes of administration including, but not limited to, oral, rectal, transmucosal, transdermal, intestinal, and parenteral. In one embodiment, B-Raf kinase inhibitor is Vemurafenib.

In one embodiment, Vemurafenib is administered orally. In one embodiment, Vemurafenib is administered in a dose ranging from 10 mg/day to 3500 mg/day. In one embodiment, Vemurafenib is administered in a dose ranging from 50 mg/day to 3000 mg/day. In one embodiment, Vemurafenib is administered in a dose ranging from 500 mg/day to 2500 mg/day. In one embodiment, Vemurafenib is administered in a dose ranging from 900 mg/day to 2000 mg/day. In one embodiment, Vemurafenib is administered in a dose of 160 mg/day. In one embodiment, Vemurafenib is administered in a dose of 200 mg/day. In one embodiment, Vemurafenib is administered in a dose of 500 mg/day. In one embodiment, Vemurafenib is administered in a dose of 960 mg/day. In one embodiment, Vemurafenib is administered in a dose of 1600 mg/day. In one embodiment, Vemurafenib is administered in a dose of 3200 mg/day.

In one embodiment, the dose of romidepsin is about 0.05 mg/m² to 5.0 mg/m² and the dose of Vemurafenib is about 500 mg/day to about 2500 mg/day. In another embodiment, the dose of romidepsin is about 0.5 mg/m² to 2.5 mg/m² and the dose of Vemurafenib is about 900 mg/day to about 2000 mg/day. In yet another embodiment, the dose of romidepsin is about 2.5 mg/m² and the dose of Vemurafenib is about 960 mg/day. In one embodiment, romidepsin and Vemurafenib are administered to the cancer patient simultaneously. In another embodiment, romidepsin is administered to the cancer patient after the patient was pretreated with Vemurafenib. In one embodiment, the cancer patient is a melanoma patient.

In another embodiment, the dose of romidepsin is about 5 mg/m$^2$ to 15.0 mg/m$^2$ and the dose of Vemurafenib is about 500 mg/day to about 2500 mg/day. In another embodiment, the dose of romidepsin is about 8 mg/m$^2$ to 12 mg/m$^2$ and the dose of Vemurafenib is about 900 mg/day to about 2000 mg/day. In yet another embodiment, the dose of romidepsin is about 10 mg/m$^2$ and the dose of Vemurafenib is about 960 mg/day. In one embodiment, romidepsin and Vemurafenib are administered to the cancer patient simultaneously. In another embodiment, romidepsin is administered to the cancer patient after the patient was pretreated with Vemurafenib. In one embodiment, the cancer patient is a melanoma patient.

In one embodiment, romidepsin is administered to a cancer patient in combination with Sorafenib.

In one embodiment, Sorafenib is administered orally. In one embodiment, Sorafenib is administered in a dose ranging from 1 mg/day to 2500 mg/day. In one embodiment, Sorafenib is administered in a dose ranging from 50 mg/day to 2000 mg/day. In one embodiment, Sorafenib is administered in a dose ranging from 75 mg/day to 1500 mg/day. In one embodiment, Sorafenib is administered in a dose ranging from 100 mg/day to 1000 mg/day. In one embodiment, Sorafenib is administered in a dose of 100 mg/day. In one embodiment, Sorafenib is administered in a dose of 200 mg/day. In one embodiment, Sorafenib is administered in a dose of 400 mg/day. In one embodiment, Sorafenib is administered in a dose of 600 mg/day. In one embodiment, Sorafenib is administered in a dose of 800 mg/day. In one embodiment, Sorafenib is administered in a dose of 1000 mg/day.

In one embodiment, the dose of romidepsin is about 0.05 mg/m$^2$ to 5.0 mg/m$^2$ and the dose of Sorafenib is about 1 mg/day to about 1500 mg/day. In another embodiment, the dose of romidepsin is about 0.5 mg/m$^2$ to 2.5 mg/m$^2$ and the dose of Sorafenib is about 100 mg/day to about 1000 mg/day. In yet another embodiment, the dose of romidepsin is about 2.5 mg/m$^2$ and the dose of Sorafenib is about 800 mg/day. In one embodiment, romidepsin and Sorafenib are administered to the cancer patient simultaneously. In another embodiment, romidepsin is administered to the cancer patient after the patient was pretreated with Sorafenib. In one embodiment, the cancer patient is a melanoma patient.

In one embodiment, the dose of romidepsin is about 5 mg/m$^2$ to 15 mg/m$^2$ and the dose of Sorafenib is about 1 mg/day to about 1500 mg/day. In another embodiment, the dose of romidepsin is about 8 mg/m$^2$ to 12 mg/m$^2$ and the dose of Sorafenib is about 100 mg/day to about 1000 mg/day. In yet another embodiment, the dose of romidepsin is about 10 mg/m$^2$ and the dose of Sorafenib is about 800 mg/day. In one embodiment, romidepsin and Sorafenib are administered to the cancer patient simultaneously. In another embodiment, romidepsin is administered to the cancer patient after the patient was pretreated with Sorafenib. In one embodiment, the cancer patient is a melanoma patient.

In one embodiment, provided herein are methods for inhibiting or preventing proliferation of drug-tolerant persisters (DTP) resistant to EGFR tyrosine kinase inhibitors or serine/threonine protein kinase B-Raf kinase inhibitors, comprising contacting the DTPs with (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are co-administered to the DTPs simultaneously. In another embodiment, the HDAC inhibitor is administered to the DTPs after pretreatment with the EGFR tyrosine kinase inhibitor or the B-Raf kinase inhibitor.

In one embodiment, provided herein are methods for inhibiting or preventing formation of colonies of drug-tolerant expanded persisters (DTEP) resistant to EGFR tyrosine kinase inhibitors or B-Raf kinase inhibitors, comprising contacting the DTEPs with (i) an EGFR tyrosine kinase inhibitor or a B-Raf kinase inhibitor, and (ii) an HDAC inhibitor. In one embodiment, the EGFR tyrosine kinase inhibitor or the B-Raf kinase inhibitor, and the HDAC inhibitor are co-administered to the DTEPs simultaneously. In another embodiment, the HDAC inhibitor is administered to the DTEPs after pretreatment with an EGFR tyrosine kinase inhibitor or a B-Raf kinase inhibitor.

In one embodiment, the cancer cells, DTPs or DTEPs are cancer cells of any origin.

In one embodiment, the cancer cell line is any cancer cell line. In another embodiment, the cancer cell line is a melanoma cancer cell line or a non-small cell lung cancer (NSCLC) cell line. In one embodiment, the melanoma cancer cell line is M14. In another embodiment, the NSCLC cancer cell line is HCC827.

In one embodiment, the EGFR tyrosine kinase inhibitor is any EGFR tyrosine kinase inhibitor. EGFR tyrosine kinase inhibitors suitable for use in the methods provided herein include, but are not limited to, Erlotinib, Getifinib, Lapatinib, Afatinib, Canertinib, Neratinib, Pelitinib, CP-724714, CUDC-101, and WZ4002. In one embodiment, the EGFR tyrosine kinase inhibitor is Erlotinib.

In one embodiment, B-Raf kinase inhibitor is any B-Raf kinase inhibitor. B-Raf kinase inhibitors suitable for use in the methods provided herein include, but are not limited to, Vemurafenib (PLX4032), Sorafenib (AZ628), Dabrafenib, PLX-4720, GDC-0879, RAF-265, and SB690885. In one embodiment, the B-Raf kinase inhibitor is Vemurafenib. In another embodiment, the B-Raf kinase inhibitor is Sorafenib.

HDAC inhibitors for use in methods provided herein include, but are not limited to, trichostatin A (TSA), Vorinostat (SAHA), Valproic Acid (VPA), romidepsin and MS-275. In one embodiment, the HDAC inhibitor is romidepsin.

In one embodiment, cells are treated with a sufficient concentration of (i) an EGFR tyrosine kinase inhibitor or a B-Raf kinase inhibitor, and (ii) an HDAC inhibitor to kill the cells. In one embodiment, a sufficient concentration of (i) an EGFR tyrosine kinase inhibitor or a B-Raf kinase inhibitor, and (ii) an HDAC inhibitor is used to prevent cell growth. In one embodiment, the cells are DTPs. In another embodiment, the cells are DTEPs. In one embodiment, the cells are in a cancer patient.

In one embodiment, in the methods provided herein romidepsin is used in the concentration that ranges from about 0.01 nM to about 100 nM. In another embodiment, the concentration of the romidepsin ranges from about 0.1 nM to about 10 nM. In another embodiment, the concentration of the romidepsin ranges from about 0.5 nM to about 5 nM. In one embodiment, the concentration of the romidepsin is about 0.1 nM, about 0.5 nM, about 1 nM, about 1.5 nM, about 2.0 nM, about 2.5 nM, about 3.0 nM, about 3.5 nM, about 4.0 nM, about 4.5 nM, or about 5.0 nM.

In one embodiment, in the methods provided herein, cells are treated with the romidepsin within a period of time from 0 days to 45 days. In one embodiment, the cells are treated with the romidepsin every three days of the 45-day cycle. In one embodiment, the cells are treated with the romidepsin on day 0, on day 3, on day 6, on day 9, on day 12, on day 15, on day 18, on day 21, on day 24, on day 27, on day 30, on day 33, on day 36, on day 39, on day 42, and on day 45 of the 45-day cycle. In one embodiment, the cells are treated with the romidepsin on day 0, on day 3, on day 6, on day 9, on day 15, on day 27, on day 33, and on day 45 of the 45-day cycle. In one embodiment, the cells are in a cancer patient.

In one embodiment, cells are treated with a drug. In one embodiment, the drug is EGFR tyrosine kinase inhibitor. In one embodiment, the EGFR tyrosine kinase inhibitor is Erlotinib. In one embodiment, the cells are in a cancer patient.

In one embodiment, the concentration of Erlotinib is about 0.1 µM to about 50 µM. In one embodiment, the concentration of Erlotinib is about 0.5 µM to about 25 µM. In one embodiment, the concentration of Erlotinib is about 1 µM to about 5 µM. In one embodiment, the concentration of Erlotinib is about 1 µM, about 2 µM, about 3 µM, about 4 µM, or about 5 µM.

In one embodiment, the drug is B-Raf kinase inhibitor. In one embodiment, the B-Raf kinase inhibitor is Vemurafenib. In another embodiment, the B-Raf kinase inhibitor is Sorafenib. In one embodiment, the cells are in a cancer patient.

In one embodiment, the concentration of Vemurafenib or Sorafenib is about 0.1 µM to about 50 µM. In one embodiment, the concentration of Vemurafenib or Sorafenib is about 0.5 µM to about 25 µM. In one embodiment, the concentration of Vemurafenib or Sorafenib is about 1 µM to about 5 µM. In one embodiment, the concentration of Vemurafenib or Sorafenib is about 1 µM, about 2 µM, about 3 µM, about 4 µM, or about 5 µM.

In one embodiment, in the methods provided herein, cells are treated with a drug within a period of time from 0 days to 45 days. In one embodiment, the drug is Erlotinib, Vemurafenib, or Sorafenib. In one embodiment, cells are treated with Erlotinib, Vemurafenib, or Sorafenib every three days of the 45-day cycle. In one embodiment, the cells are treated with Erlotinib, Vemurafenib, or Sorafenib on day 0, on day 3, on day 6, on day 9, on day 12, on day 15, on day 18, on day 21, on day 24, on day 27, on day 30, on day 33, on day 36, on day 39, on day 42, and on day 45 of the 45-day cycle. In one embodiment, cells are treated with Vemurafenib or Sorafenib on day 0, on day 3, on day 6, on day 9, on day 15, on day 27, on day 33, and on day 45 of the 45-day cycle. In one embodiment, cells are treated with Erlotinib on day 0, on day 3, on day 6, on day 9, on day 15, on day 19, on day 22, and on day 27 of the 45-day cycle. In one embodiment, the cells are in a cancer patient.

In one embodiment, in the methods provided herein, cells are treated with a combination of the romidepsin and a drug. In one embodiment, the drug and an HDAC inhibitor are coadministered to the cells simultaneously. In another embodiment, an HDAC inhibitor is administered to the cells after pretreatment with the drug. In one embodiment, the drug is Erlotinib. In another embodiment, the drug is Vemurafenib. In yet another embodiment, the drug is Sorafenib. In one embodiment, the cells are in a cancer patient.

In one embodiment, cells are treated with the romidepsin in a concentration from about 0.5 nM to about 5 nM in combination with Erlotinib in the concentration of about 1 µM to about 5 µM on day 0, on day 3, on day 6, on day 9, on day 15, on day 19, on day 22, and on day 27 of the 45-day cycle. In one embodiment, Erlotinib and romidepsin are added to the cells simultaneously. In another embodiment, romidepsin is added to the cells after pretreatment with Erlotinib. In one embodiment, the cells are non-small cell lung cancer cell line HCC827 or non-small cell lung cancer cells. In one embodiment, the cells are in a cancer patient.

In one embodiment, the cells are treated with romidepsin in a concentration from about 0.5 nM to about 5 nM in combination with Vemurafenib in a concentration of about 1 µM to about 5 µM on day 0, day 3, day 6, day 9, day 15, day 27, day 33, and day 45 of the 45-day cycle. In one embodiment, Vemurafenib and romidepsin are added to the cells simultaneously. In another embodiment, romidepsin is added to the cells after pretreatment with Vemurafenib. In one embodiment, the cells are melanoma cell line M14 or melanoma cells. In one embodiment, the cells are in a cancer patient.

In one embodiment, the cells are treated with romidepsin in a concentration from about 0.5 nM to about 5 nM in combination with Sorafenib in a concentration of about 1 µM to about 5 µM on day 0, day 3, day 6, day 9, day 15, day 27, day 33, and day 45 of the 45-day cycle. In one embodiment, Sorafenib and romidepsin are added to the cells simultaneously. In another embodiment, romidepsin is added to the cells after pretreatment with Sorafenib. In one embodiment, the cells are melanoma cell line M14 or melanoma cells. In one embodiment, the cells are in a cancer patient.

Compositions

Provided herein are pharmaceutical compositions comprising romidepsin as an active ingredient, including an enantiomer, a mixture of enantiomers, a mixture of two or more diastereomers, a tautomer, a mixture of two or more tautomers, or an isotopic variant thereof or a pharmaceutically acceptable salt, solvate, hydrate, or prodrug; in combination with a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate.

The pharmaceutical compositions comprising romidepsin can be formulated in various dosage forms for oral and parenteral administration.

In one embodiment, the pharmaceutical compositions are provided in a dosage form for oral administration, which comprise romidepsin, including an enantiomer, a mixture of enantiomers, a mixture of two or more diastereomers, a tautomer, a mixture of two or more tautomers, or an isotopic variant thereof; and a pharmaceutically acceptable salt, solvate, hydrate, or prodrug thereof; and one or more pharmaceutically acceptable excipients or carriers.

In another embodiment, the pharmaceutical compositions are provided in a dosage form for parenteral administration, which comprise romidepsin including an enantiomer, a mixture of enantiomers, a mixture of two or more diastereomers, a tautomer, a mixture of two or more tautomers, or an isotopic variant thereof; and a pharmaceutically acceptable salt, solvate, hydrate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone.

Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve a plurality of functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylceluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

Romidepsin Formulation

In one embodiment, romidepsin is formulated for injection as a sterile lyophilized white powder and is supplied in a single-use vial containing 10 mg romidepsin and 20 mg povidone, USP. The diluent is a sterile clear solution and is supplied in a single-use vial containing a 2 ml deliverable volume. The diluent for romidepsin contains 80% (v/v) propylene glycol, USP and 20% (v/v) dehydrated alcohol, USP. Romidepsin is supplied as a kit containing two vials.

Romidepsin for injection is intended for intravenous infusion after reconstitution with the supplied Diluent and after further dilution with 0.9% Sodium Chloride, USP.

Erlotinib Formulation

In one embodiment, Erlotinib is formulated as a tablet containing 25 mg, 100 mg or 150 mg of Erlotinib and the following inactive ingredients: lactose monohydrate, hypromellose, hydroxypropyl cellulose, magnesium stearate, microcrystalline cellulose, sodium starch glycolate, sodium lauryl sulfate and titanium dioxide. The tablets also contain trace amounts of color additives, including FD&C Yellow #6 (25 mg only) for product identification.

Vemurafenib Formulation

In one embodiment, Vemurafenib is formulated as a tablet containing 240 mg of vemurafenib. The inactive ingredients of a tablet core: hypromellose acetate succinate, croscarmellose sodium, colloidal silicon dioxide, magnesium stearate, and hydroxypropyl cellulose. The inactive ingredients of coating: pinkish white: poly(vinyl alcohol), titanium dioxide, polyethylene glycol 3350, talc, and iron oxide red.

Sorafenib Formulation

In one embodiment, each red, round film-coated tablet contains sorafenib tosylate (274 mg) equivalent to 200 mg of sorafenib and the following inactive ingredients: croscarmellose sodium, microcrystalline cellulose, hypromellose, sodium lauryl sulphate, magnesium stearate, polyethylene glycol, titanium dioxide and ferric oxide red.

EXAMPLES

Materials and Methods

The M14 melanoma and HCC827 non-small cell lung cancer cell (NSCLC) cell lines were purchased from American Type Culture Collection (ATCC; Manassas, Va.). Cells were cultured at 37° C./5% $CO_2$ in RPMI-1640 medium (ATCC) supplemented with 10% FBS. AZ628 and Erlotinib were purchased from Selleck Chemicals (Houston, Tex.) and reconstituted in DMSO to 20 mM. Romidepsin (Celgene Corporation) was reconstituted in DMSO to 10 µM. All drugs were stored at −30° C.

Drug Treatment and Cell Viability Assay

Cells were seeded at $1.0 \times 10^4$ cells/well into 24-well plates (using 1 mL of media per well) and allowed to adhere for 24 hours prior to treatment (in duplicate or triplicate wells) with DMSO or romidepsin alone, or in combination with a drug (2 µM Erlotinib for HCC827 or 2 µM AZ628 for M14). Romidepsin was used at a final concentration of 1 nM for HCC827 cells and 0.5 nM for M14 cells. Conditioned media were replaced with fresh drug-containing media every three days ("continuous Q3D" schedule). The Q3D schedule was evaluated continuously over a period of 27-45 days, and also for shorter durations ranging from 3-21 days. In romidepsin wash-out experiments, AZ628/Erlotinib- and romidepsin-containing conditioned media were aspirated from cells 6 hours after addition of drugs and replaced with vehicle- or AZ628/ERL-containing media.

Cell viability was monitored periodically over 27-45 days using CellTiter-Glo (CTG). On select days, an equal volume (1 mL) of CTG was added to each well of the 24-well plates. The plates, wrapped with aluminum foil, were incubated on a shaking platform for 10 minutes. A 200 µL aliquot from each well was transferred to a new well of 96-well plates. The SpectraMax L (Molecular Devices; Sunnyvale, Calif.) was used to measure luminescence.

Example 1

Figure 3A:
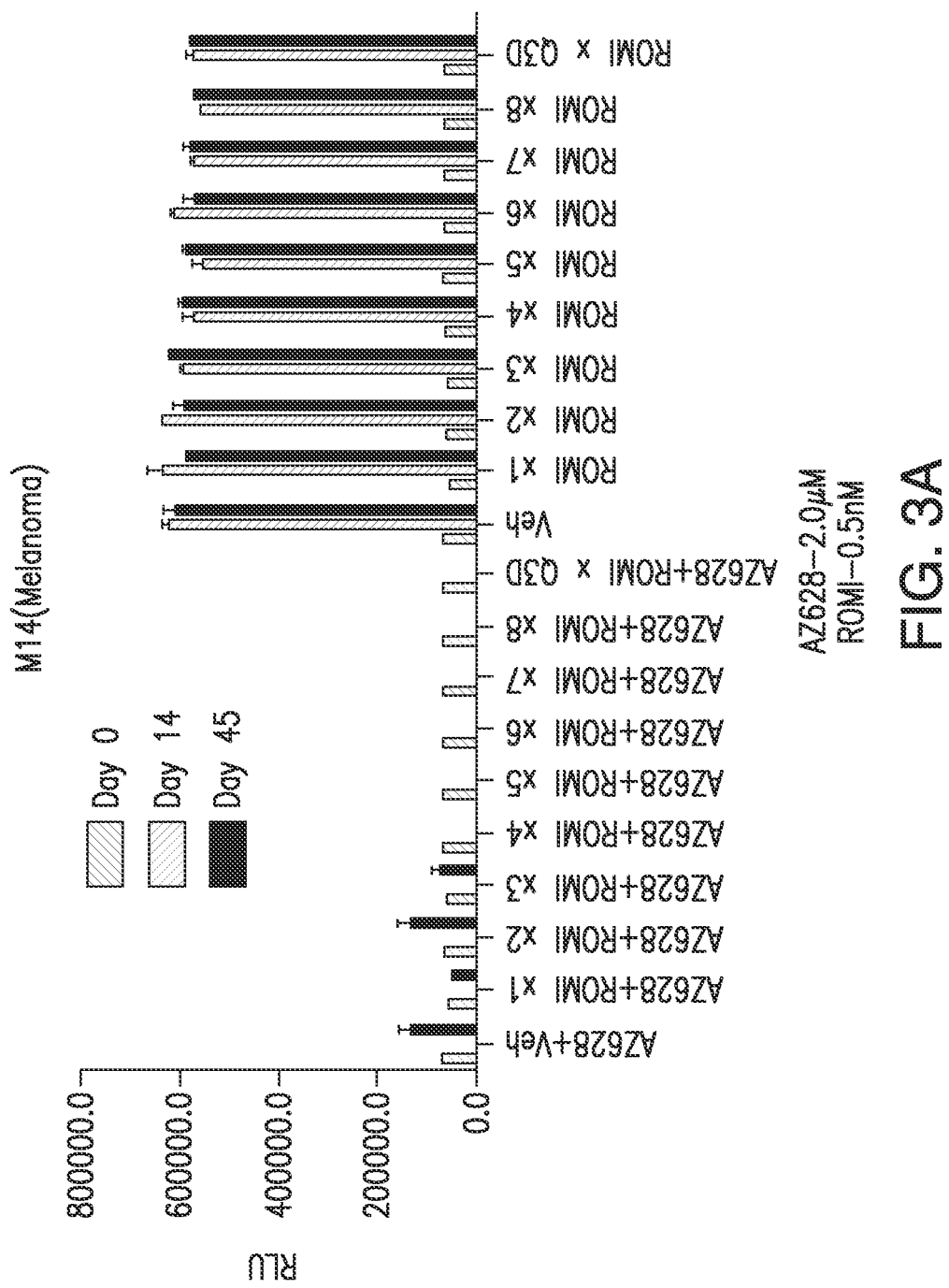
FIGS. 3A and 3B depict the effect of a limited number of romidepsin doses on prevention of DTEP growth in melanoma cell line M14. Romidepsin was used at a concentration of 0.5 nM, and AZ628 was used at a concentration of 2 µM.
Figure 3B:
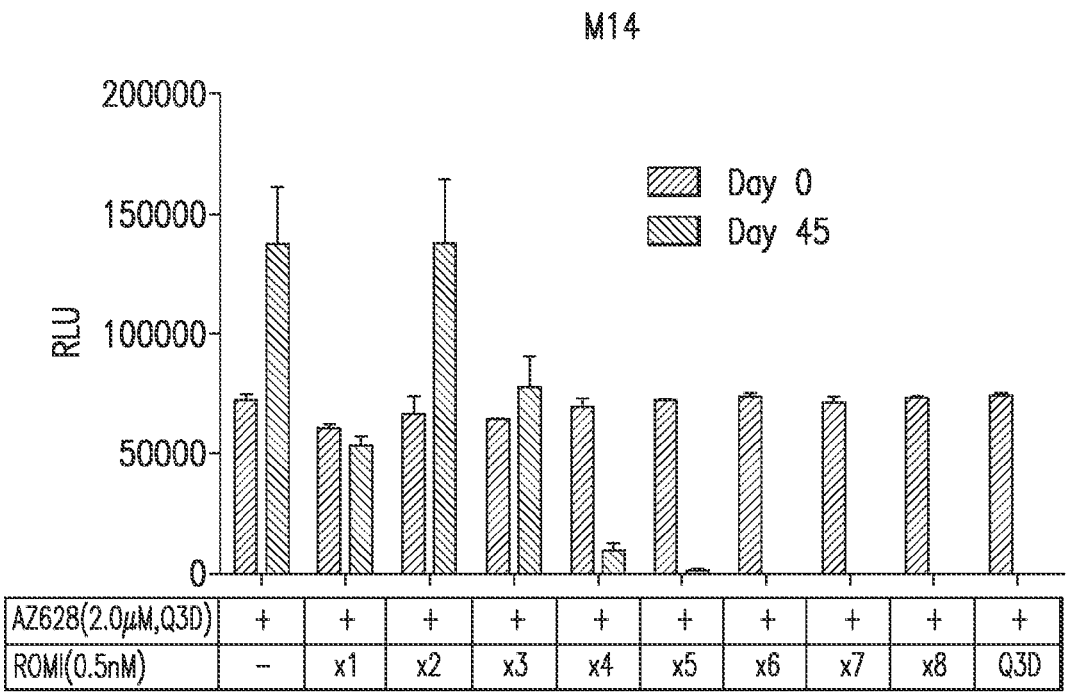
Figure 4A:
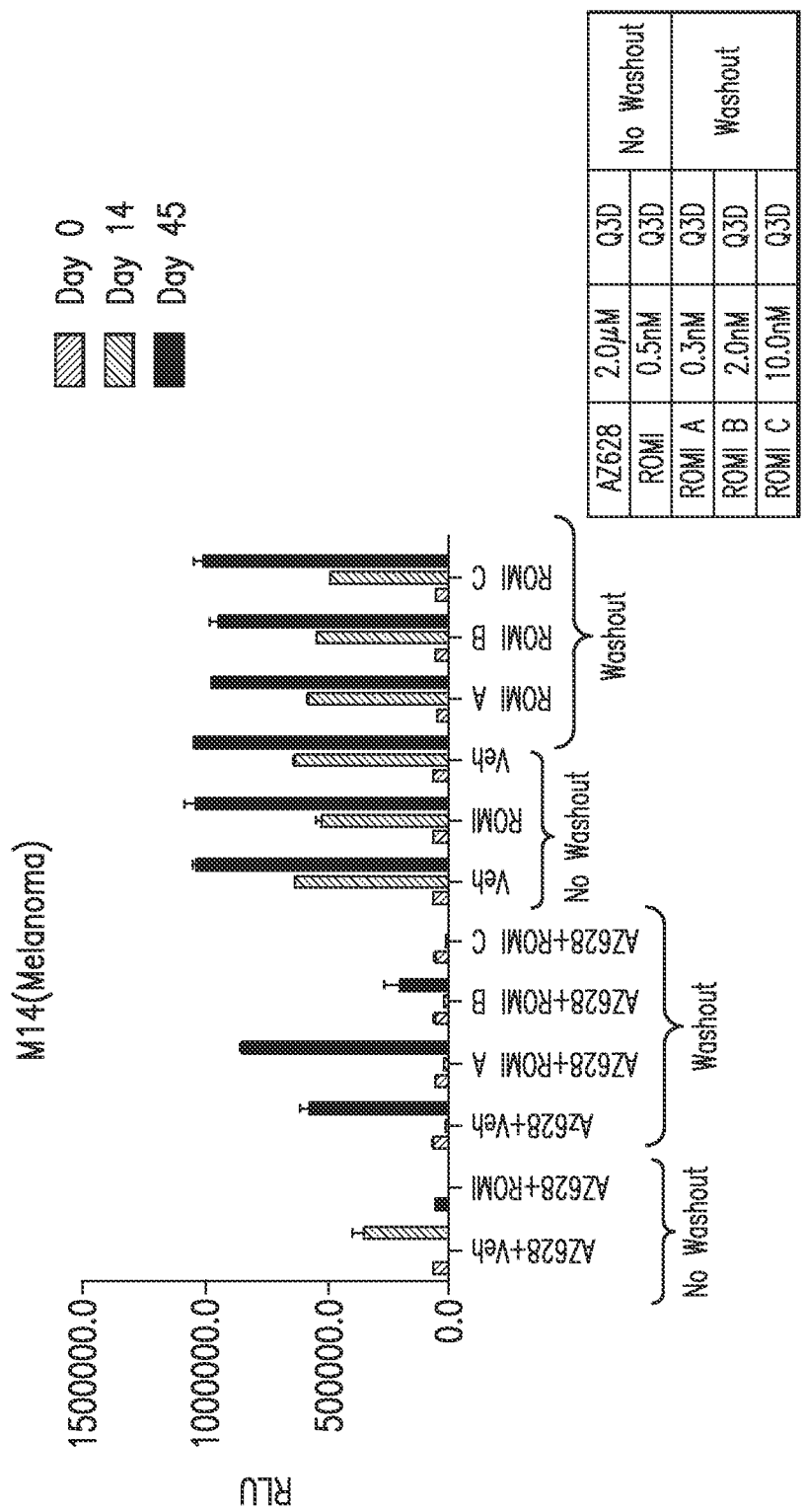
FIG. 4A shows the effect of 6-hour romidepsin exposure (wash-out) on prevention of DTEP growth in a melanoma cell line (M14). Romidepsin and AZ628 were added to the cell culture every 3 days at a concentration of 0.5 nM and 2 µM, respectively, with no-washout. In the wash-out experiment, AZ628- and romidepsin-containing conditioned media were aspirated from cells 6 hours after addition of drugs and replaced with AZ628-containing media. Romidepsin was used in the concentration of 0.5 nM (A), 2 nM (B), or 10 nM (C).

Romidepsin Prevents the Emergence of Drug-Tolerant Cancer Cells in Melanoma Cell Lines Massive cell death was observed after 9 days of treatment of melanoma (M14) cells with high concentrations (100× $IC_{50}$) of AZ628. With continued treatments with AZ628, it was observed that a few remaining drug tolerant persisters (DTPs) were able to proliferate to form drug tolerant expanded persisters (DTEPs), yielding a large population of AZ628-resistant cells. "Continuous" co-treatment of cancer cells with AZ628 in combination with sub-lethal concentration of romidespin prevented the emergence of DTEPs (FIG. 1). It was also shown that romidepsin prevented the emergence of DTEP in M14 melanoma cells treated with AZ628 based on a reduced schedule (every 3 days for 2 weeks). 5 doses of romidepsin were sufficient to prevent the emergence of DTEP melanoma M14 cells treated with AZ628. The results are shown in FIGS. 3A and 3B. Short (6-hour) exposure to higher romidepsin concentration on the "continuous" schedule was also sufficient to prevent DTEP growth in melanoma cells (FIG. 4A).

The obtained results demonstrated that romidepsin prevented the DTEP emergence in M14 melanoma cells. Dosing romidepsin for 2 weeks every 3 days (5 doses) and 6-hour exposure were sufficient the prevent the emergence of cells resistant to AZ628. These results showed that the co-treatment with romidepsin prevents resistance to AZ628 in melanoma cells and provides guidance to the dose and schedule requirements for clinical evaluation.

Example 2

Figure 2:
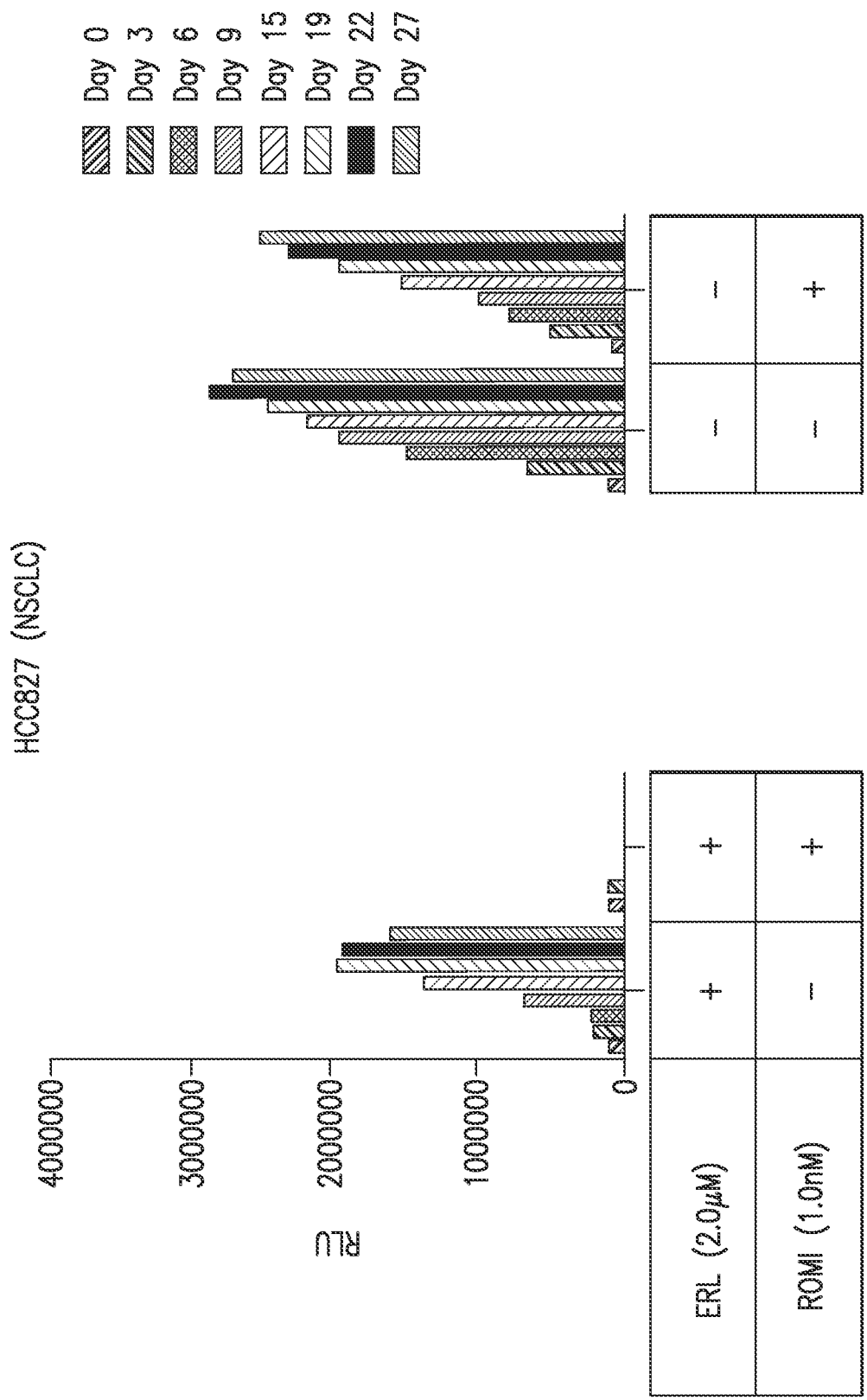
FIG. 2 shows the effect of the combination of Erlotinib and romidepsin on DTEP emergence in a non-small cell lung cancer cell line (HCC827). Both agents were added to the cells every 3 days during the "continuous" schedule (27 days) at a concentration of 2 µM for Erlotinib and 1.0 nM for romidepsin. Cell viability was measured on select days using CellTiter-Glo.
Figure 3C:
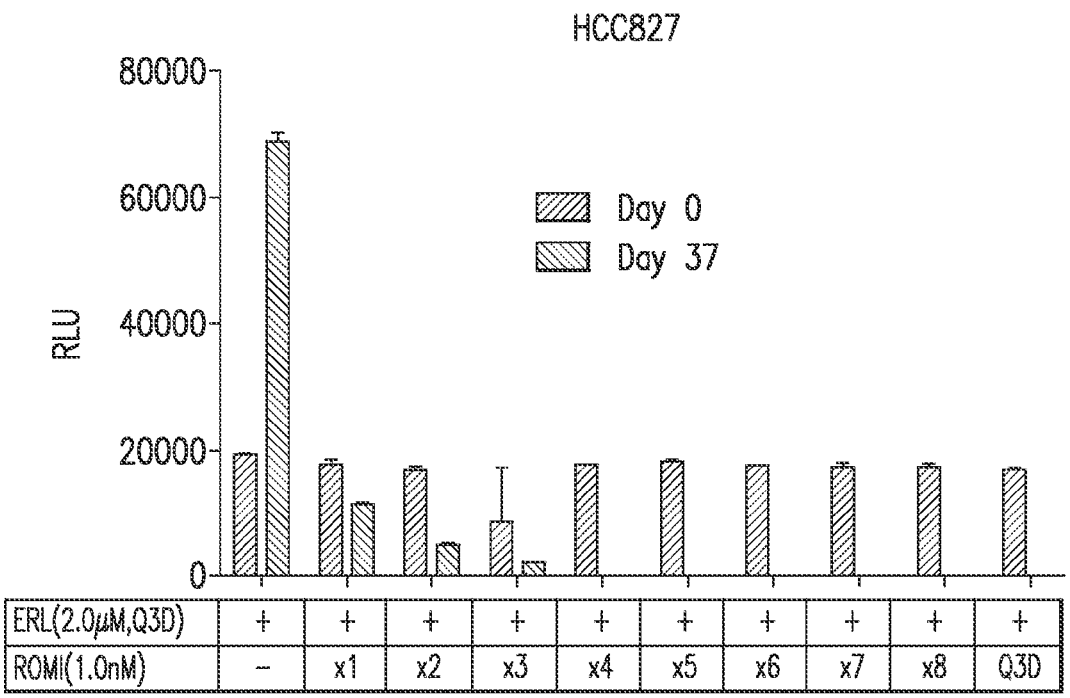
FIG. 3C depicts the effect of a limited number of romidepsin doses on the prevention of DTEP growth in a non small cell lung cancer cell line (HCC827). Romidepsin was used at a concentration of 1.0 nM, and Erlotinib was used at a concentration of 2 µM.
Figure 4B:
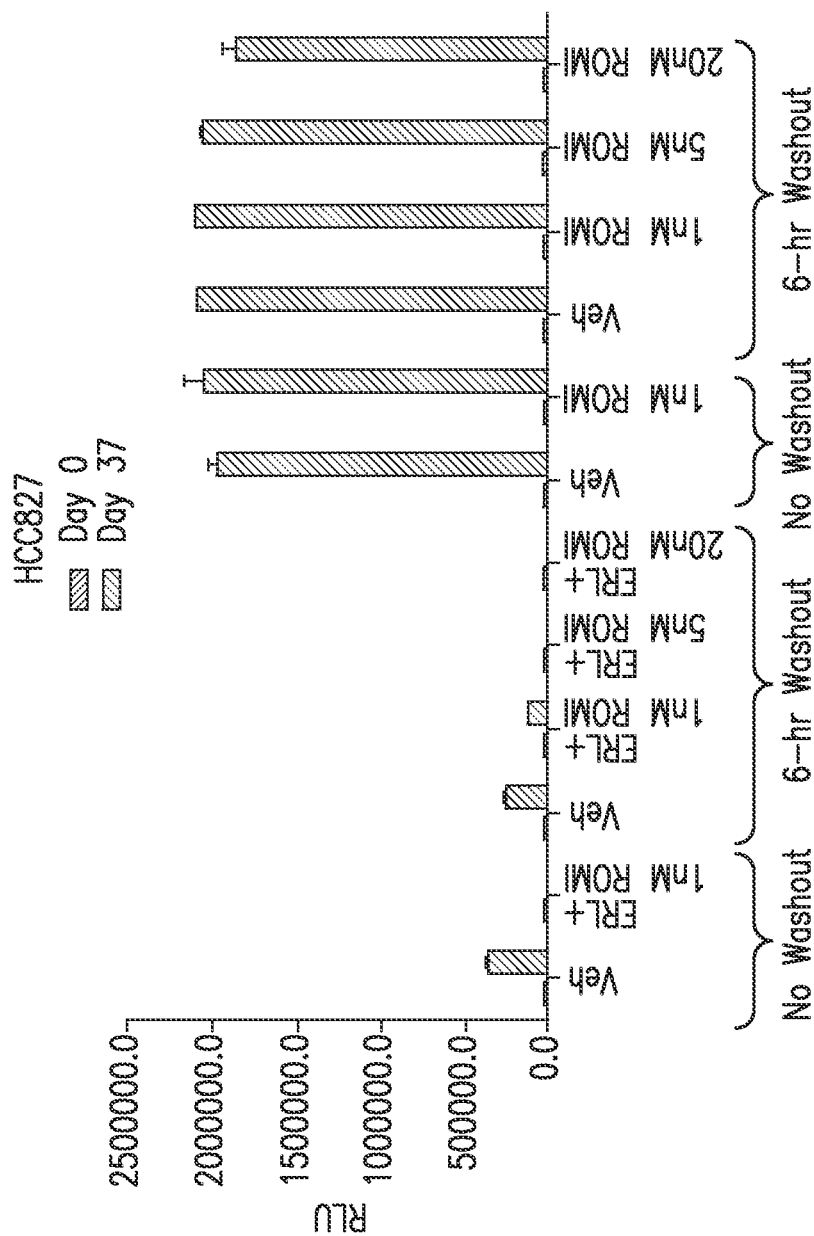
FIG. 4B shows the effect of 6-hour romidepsin exposure (wash-out) on prevention of DTEP growth in a non small cell lung cancer cell line (HCC827). Romidepsin and Erlotinib were added to the cell culture every 3 days at a concentration of 1.0 nM and 2 µM, respectively, with no-washout. In the wash-out experiment, Erlotinib- and romidepsin-containing conditioned media were aspirated from cells 6 hours after addition of drugs and replaced with Erlotinib-containing media. Romidepsin was used at a concentration of 1, 5, and 20 nM.

Romidepsin Prevents the Emergence of Drug-Tolerant Cancer Cells in Non-Small Cell Lung Cancer Cell Lines Massive cell death was observed after 9 days of treatment of NSCLC cells with high concentrations ($100 \times IC_{50}$) of Erlotinib. With continued treatments with Erlotinib, it was observed that some remaining NSCLC cells (DTPS) were able to proliferate into DTEPs, yielding a large population of Erlotinib-resistant cells. "Continuous" co-treatment of NSCLC cells with Erlotinib in combination with sub-lethal concentration of romidepsin prevented the emergence of DTEPs. The results are shown in FIG. 2. It was also shown that romidepsin prevented the emergence of DTEPs in NSCLC cells treated with Erlotinib based on a reduced schedule (every 3 days for 2 weeks). Four (4) doses of romidepsin were sufficient to prevent the emergence of DTEP NSCLC HCC827 cells treated with Erlotinib. The results are shown in FIG. 3C. Short (6-hour) exposure to higher romidepsin concentration on the "continuous" schedule was also sufficient to prevent DTEP growth in NSCLC HCC827 cells (FIG. 4B).

The obtained results demonstrated that romidepsin prevented the DTEP emergence in NSCLC HCC827 cells. Dosing romidepsin for 2 weeks every 3 days (4 doses) and 6-hour exposure were sufficient to prevent the emergence of cells resistant to Erlotinib. These results indicated that the co-treatment with romidepsin prevents resistance to Erlotinib in NSCLC cells and provides guidance to the dose and schedule requirements for clinical evaluation.

Example 3

Delayed Addition of Romidepsin Prevents the Emergence of Drug-Tolerant Cancer Cells in Non-Small Cell Lung Cancer Cell Lines HCC827 cells were seeded at $1.0 \times 10^4$ cells/well into 24-well plates (using 1 mL of medium per well) and allowed to adhere for 24 hours prior to treatment (in duplicate or triplicate wells) with DMSO (vehicle) and 2 µM Erlotinib. Conditioned medium was replaced with fresh drug-containing medium every three days. Starting on day 12, the drug-containing medium also included 1 nM romidepsin. Cell viability was monitored on days 0, 15, and 37 using CellTiter-Glo (CTG).

Figure 5:
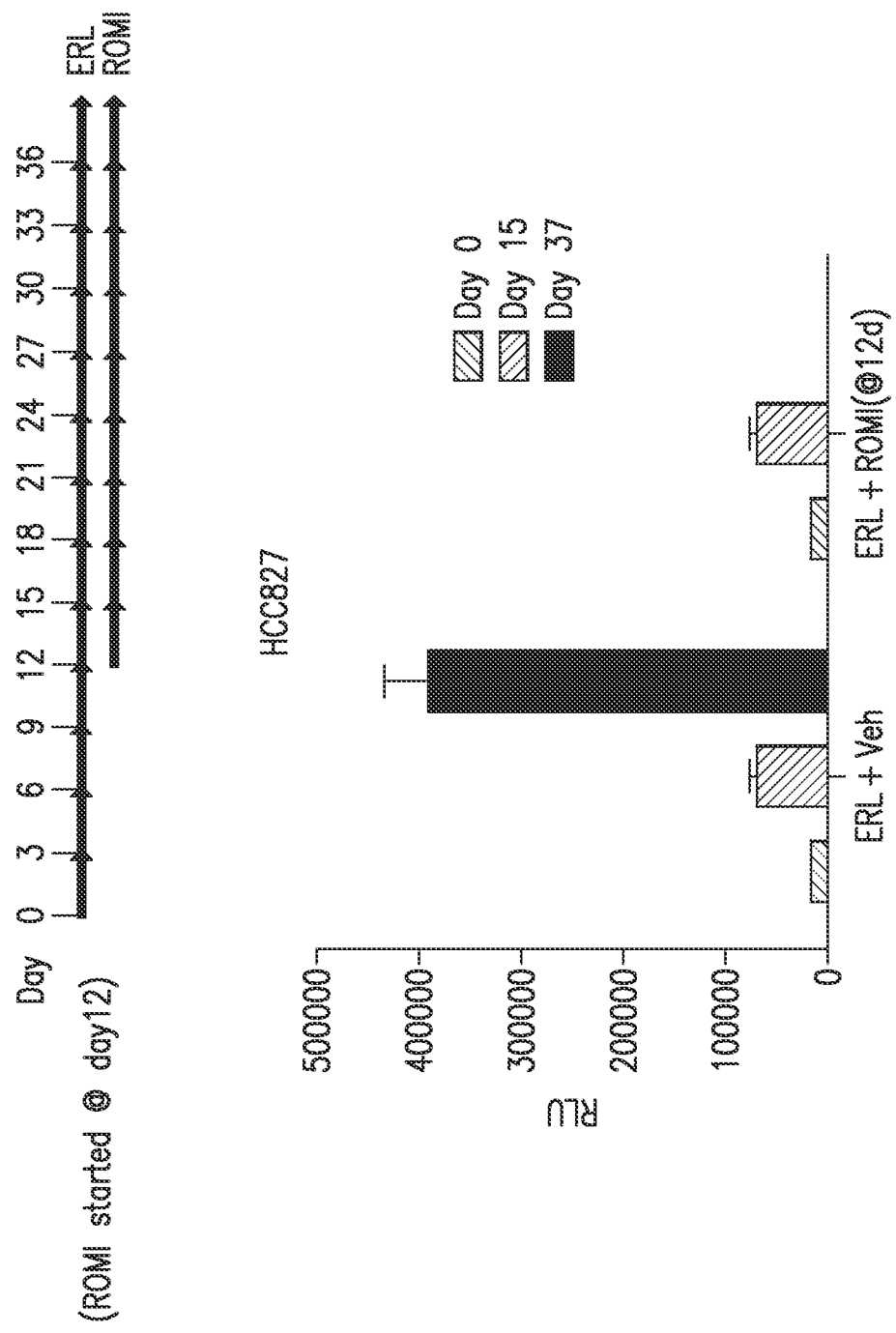
FIG. 5 shows the effect of addition of romidepsin on prevention of emergence of DTEP after pretreatment with Erlotinib in a non-small cell lung cancer cell line (HCC827). Conditioned medium was replaced with fresh drug-containing medium every three days. On day 12, romidepsin in the concentration of 1 nM was added to the drug-containing medium.

The results of these experiments are shown in FIG. 5. These results indicate that addition of romidepsin after pretreatment with Erlotinib eliminated Erlotinib-resistant HCC827 cells.

All publications, patents, and patent applications mentioned in this specification are herein incorporated by reference to the same extent as if each individual publication, patent, or patent application was specifically and individually indicated to be incorporated by reference.

The present disclosure has been described above with reference to exemplary embodiments. However, those skilled in the art, having read this disclosure, will recognize that changes and modifications may be made to the exemplary embodiments without departing from the scope of the present disclosure. The changes or modifications are intended to be included within the scope of the present disclosure, as expressed in the following claims.

What is claimed:

1. A method of treating melanoma in a patient by overcoming resistance of the melanoma cells to a serine/threonine protein kinase B-Raf (B-Raf) kinase inhibitor, comprising administering to the melanoma patient a histone deacetylase (HDAC) inhibitor, wherein the B-Raf kinase inhibitor is sorafenib, wherein the HDAC inhibitor is romidepsin, and wherein romidepsin is administered to the patient after pretreatment with sorafenib.

2. The method of claim 1, wherein the dose of romidepsin is in the range of between 10 $mg/mm^2$ and 14 $mg/mm^2$.

3. The method of claim 1, wherein the dose of sorafenib is in the range of between 100 mg/day and 1000 mg/day.

4. A method for overcoming resistance of melanoma cells in a patient to a-B-Raf kinase inhibitor, comprising administering to the melanoma patient an HDAC inhibitor, wherein the B-Raf kinase inhibitor is sorafenib, wherein the HDAC inhibitor is romidepsin, and wherein romidepsin is administered to the patient after pretreatment with sorafenib.

5. The method of claim 4, wherein romidepsin is in the range of between 10 $mg/mm^2$ and 14 $mg/mm^2$.

6. The method of claim 4, wherein the dose of sorafenib is in the range of between 100 mg/day and 1000 mg/day.

* * * * *